(12) United States Patent
Li et al.

(10) Patent No.: US 10,494,334 B2
(45) Date of Patent: Dec. 3, 2019

(54) COMPOUNDS TO INHIBIT CALCIUM/CALMODULIN DEPENDENT PROTEIN KINASE II AND APPLICATIONS THEREOF

(71) Applicant: ACADEMIA SINICA, Taipei (TW)

(72) Inventors: Wen-Shan Li, Taipei (TW); Yi-Ling Lin, Taipei (TW); Wei-Chia Chen, Taipei (TW); Yogy Simanjuntak, Yogyakarta (ID)

(73) Assignee: ACADEMIA SINICA, Taipei (TW)

( * ) Notice: Subject to any disclaimer, the term of this patent is extended or adjusted under 35 U.S.C. 154(b) by 0 days.

(21) Appl. No.: 16/359,554

(22) Filed: Mar. 20, 2019

(65) Prior Publication Data

US 2019/0300475 A1 Oct. 3, 2019

Related U.S. Application Data

(60) Provisional application No. 62/649,253, filed on Mar. 28, 2018.

(51) Int. Cl.

| | |
|---|---|
| *C07C 311/21* | (2006.01) |
| *A61P 25/28* | (2006.01) |
| *A61P 25/16* | (2006.01) |
| *A61P 25/08* | (2006.01) |
| *A61P 35/00* | (2006.01) |
| *A61P 31/14* | (2006.01) |
| *A61P 9/10* | (2006.01) |
| *A61P 9/06* | (2006.01) |
| *A61P 9/04* | (2006.01) |

(52) U.S. Cl.
CPC .............. *C07C 311/21* (2013.01); *A61P 9/04* (2018.01); *A61P 9/06* (2018.01); *A61P 9/10* (2018.01); *A61P 25/08* (2018.01); *A61P 25/16* (2018.01); *A61P 25/28* (2018.01); *A61P 31/14* (2018.01); *A61P 35/00* (2018.01); *C07C 2601/04* (2017.05); *C07C 2601/08* (2017.05); *C07C 2601/18* (2017.05); *C07C 2603/74* (2017.05)

(58) Field of Classification Search
CPC ........ C07C 311/21; A61P 25/28; A61P 25/16; A61P 25/08; A61P 35/00; A61P 31/14; A61P 9/10; A61P 9/06; A61P 9/04
See application file for complete search history.

(56) References Cited

PUBLICATIONS

Zhao et al., 2017, caplus an 2017:424564.*
Wagnon et al., 1993, caplus an 1993:539091.*
Simanjuntak et al., "Japanese Encephalitis Virus Exploits Dopamine D2 Receptor-phospholipase C to Target Dopaminergic Human Neuronal Cells", Frontiers in Microbiology, Apr. 11, 2017, vol. 8, Article 651.

* cited by examiner

*Primary Examiner* — Sun Jae Yoo
(74) *Attorney, Agent, or Firm* — WPAT, PC

(57) ABSTRACT

Provided are novel benzenesulfonamide compounds that inhibit calcium/calmodulin-dependent protein kinase II (CaMKII) and pharmaceutical compositions containing the benzenesulfonamide compounds. Also provided are methods of using the benzenesulfonamide compounds to treat diseases or conditions that are associated with CaMKII activity, such as a flavivirus infection.

7 Claims, 20 Drawing Sheets

Specification includes a Sequence Listing.

5

6

7

8

9

10

11

12

13

14

15

16

COMPOUNDS TO INHIBIT CALCIUM/CALMODULIN DEPENDENT PROTEIN KINASE II AND APPLICATIONS THEREOF

CROSS-REFERENCES TO RELATED APPLICATIONS

This application claims priority of Provisional Application No. 62/649,253, filed on Mar. 28, 2018, the content of which is incorporated herein in its entirety by reference.

BACKGROUND OF THE INVENTION

1. Field of the Invention

The present invention relates to compounds that inhibit calcium/calmodulin-dependent protein kinase II (CaMKII) and applications thereof. Particularly, the present invention relates to novel benzenesulfonamide derivatives and treatment methods using the same as CaMKII inhibitors.

2. The Prior Art

Calcium/calmodulin-dependent protein kinase II (CaMKII) is a serine/threonine-specific protein kinase whose activity is regulated by the calcium and calmodulin complex. Ubiquitously expressed in various tissues, CaMKII plays a distinct role in neurons, cardiomyocytes, endothelial and immune cells. An elevated CaMKII activity serves as a key target in the etiology of cardiovascular and neurological diseases. CaMKII has also been reported as responsible for cancer progression. Moreover, one recent study has indicated the role of CaMKII in mediating cell binding and/or entry of Japanese encephalitis virus (JEV), a member of Flaviviridae (Simanjuntak et al., *Front Microbiol* 2017, 8: 651). Pharmaceutical companies are now competing to develop safe and effective CaMKII inhibitors. However, the potential role of CaMKII inhibitor in flavivirus infection remains unknown.

Dengue virus (DENV) and Zika virus (ZIKV) are emerging mosquito-borne flaviviruses that pose threats to global public health. DENV infection in humans can cause a wide spectrum of clinical features from mild dengue fever to severe dengue hemorrhagic fever and life-threatening dengue shock syndrome. A recent study suggested an increased prevalence of DENV infection to 390 million cases per year. The mortality rate has been successfully controlled; however, recurrent dengue outbreak has significant socio-economic impact in epidemic countries. Likewise, although the case fatality with ZIKV infection is low, the infection has been linked to Guillain-Barré syndrome and birth defects including microcephaly. ZIKV infection has created a public health emergency of international concern. It is reported that about 4300 infants born with microcephaly during the outbreak in Brazil.

DENV and ZIKV are small enveloped viruses with a positive-sense RNA genome that is about 11 kb and encodes a polyprotein that is processed to three structural proteins, namely capsid, premembrane (prM), and envelope (E), and seven nonstructural proteins termed NS1, NS2A, NS2B, NS3, NS4A, NS4B, and NS5, respectively. Viral infection initiates from binding to cell surface receptors through the major structural envelope protein and uses endocytosis for entry into cells. The internalized virions undergo acid-induced conformational changes and membrane fusion to release the viral genome. Translation of viral RNA produces proteins required for viral RNA replication through RNA-dependent RNA polymerization. The assembly of viral RNA and viral proteins generates the mature viral particle, which is then released through the cellular secretory pathway.

Antiviral drugs and vaccines are two major means to control viral diseases. Currently, there is no approved antiviral drug or vaccines for DENV and ZIKV infections. Vaccine development against these flaviviruses recently has been challenged because preexisting antibodies that bind to E or prM of DENV or ZIKV have been shown to enhance subsequent viral infection of monocytes in immunized individuals. For antiviral drug development, both viral and cellular proteins essential for viral replication serve as potential targets. As mentioned, it remains to be elucidated whether CaMKII is a suitable antiviral target.

SUMMARY OF THE INVENTION

The present invention is based on an unexpected finding that the newly designed benzenesulfonamide derivatives act as CaMKII inhibitors and are useful in treating diseases associated with CaMKII activity, such as DENV and ZIKV infections.

Accordingly, the present invention provides a compound which is represented by formula (I):

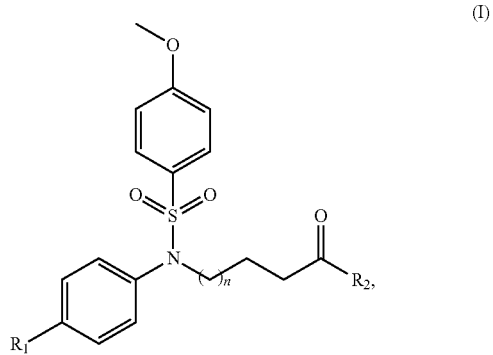

wherein $R_1$ is hydrogen, cycloalkyl having 3 to 7 carbon ring atoms, heterocycle having 2 to 8 carbon ring atoms and at least one heteroatom selected from the group consisting of nitrogen, oxygen, and sulfur, or aryl having 2 to 3 rings each with 4 to 6 ring atoms; or $R_1$ together with the phenyl ring to which $R_1$ is attached form a fused bicyclic carbocycle having 8 to 10 carbon ring atoms; $R_2$ is cycloalkyl having 4 to 10 carbon ring atoms, or heterocycle selected from the group consisting of thiazole, imidazole, tetrazole, imidazolidine, imidazoline, isoxazole, and benzimidazole; and n is 1, 2, 4, or 6.

In one embodiment of the present invention, $R_1$ is hydrogen and n is 1. In one preferred embodiment, the compound is represented by one of the following formulas:

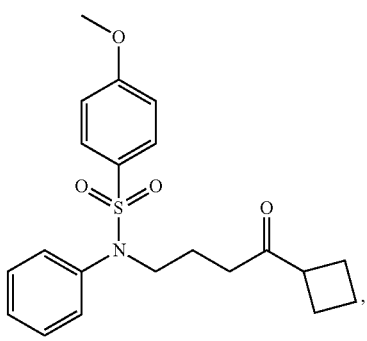

7

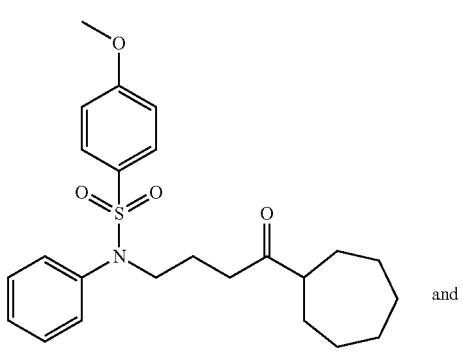

8

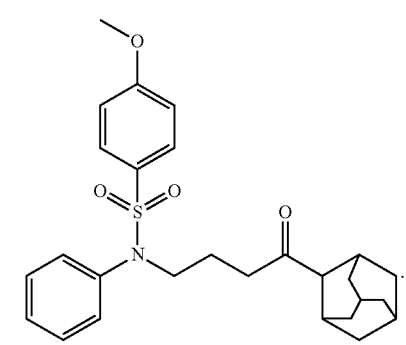

9

10

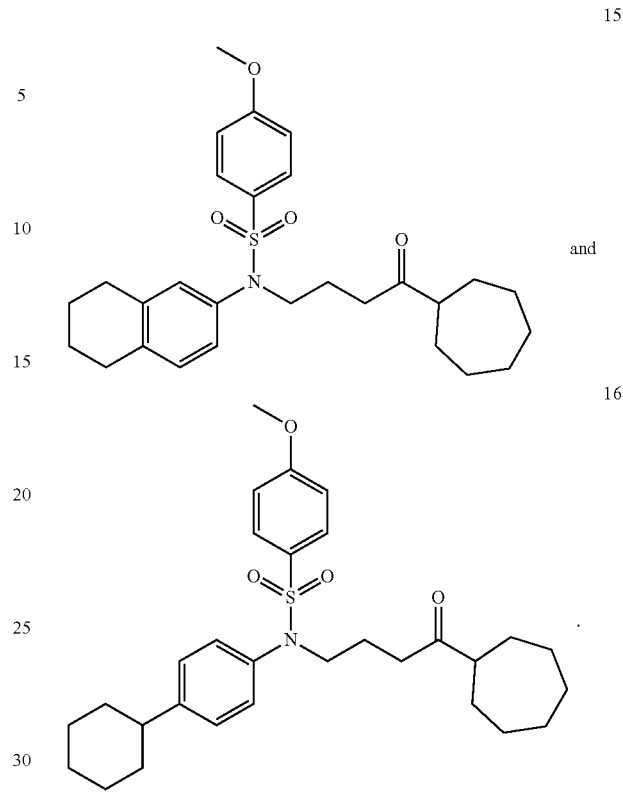

15 and

16

In another embodiment of the present invention, R₁ is hydrogen; R₂ is cycloheptyl; and n is 2, 4, or 6.

In still another embodiment of present invention, R₂ is cycloheptyl and n is 1. In one preferred embodiment, the compound is represented by one of the following formulas:

In another aspect, the present invention provides a pharmaceutical composition, including at least one compound defined above and a pharmaceutically acceptable carrier.

In one further aspect, the present invention provides a method of inhibiting CaMKII activity in a cell, including contacting the cell with an effective amount of the compound of formula (I) or the pharmaceutical composition containing the same.

In one further aspect, the present invention provides a method of treating a disease or condition associated with CaMKII activity in a subject in need thereof, including administering to the subject an effective amount of the compound of formula (I) or the pharmaceutical composition containing the same.

The disease or condition associated with CaMKII activity is a disease or condition having a causative relationship with increased CaMKII activity in specific cells or tissues of the subject in need compared to a non-diseased subject. Such disease or condition also includes the symptoms caused by and/or exacerbated by CaMKII activity. In one embodiment, said disease or condition is a flavivirus infection, wherein the flavivirus is selected from the group consisting of dengue virus, Zika virus, Japanese encephalitis virus, West Nile virus, yellow fever virus, and combinations thereof. In another embodiment, said disease or condition is a cancer such as lung cancer, breast cancer, prostate cancer, and colon cancer. In still another embodiment, said disease or condition is a cardiovascular disease or condition such as arrhythmia, ischemia-reperfusion injury, and heart failure. In still another embodiment, said disease or condition is a neurological disease such as Alzheimer's disease, Parkinson's disease, and epilepsy.

In one further aspect, the present invention provides a method of reducing entry of a flavivirus into a cell, including contacting the cell with an effective amount of the compound of formula (I).

In one embodiment of the present invention, the flavivirus is selected from the group consisting of dengue virus, Zika virus, Japanese encephalitis virus, West Nile virus, yellow fever virus, and combinations thereof.

The present invention discloses that the compound of formula (I) is effective in inhibiting protein phosphorylation by CaMKII and improves the survival of DENV or ZIKV-infected animals. Therefore, the present invention provides a new strategy to treat diseases or conditions associated with CaMKII activity.

The present invention is further explained in the following examples. It is understood that the examples given below do not limit the scope of the invention, and it will be evident to those skilled in the art that modifications can be made without departing from the scope of the appended claims.

BRIEF DESCRIPTION OF THE DRAWINGS

The present invention will be apparent to those skilled in the art from the following detailed description of the preferred embodiments, with reference to the attached drawings, in which.

DETAILED DESCRIPTION OF THE PREFERRED EMBODIMENT

Figure 1A:
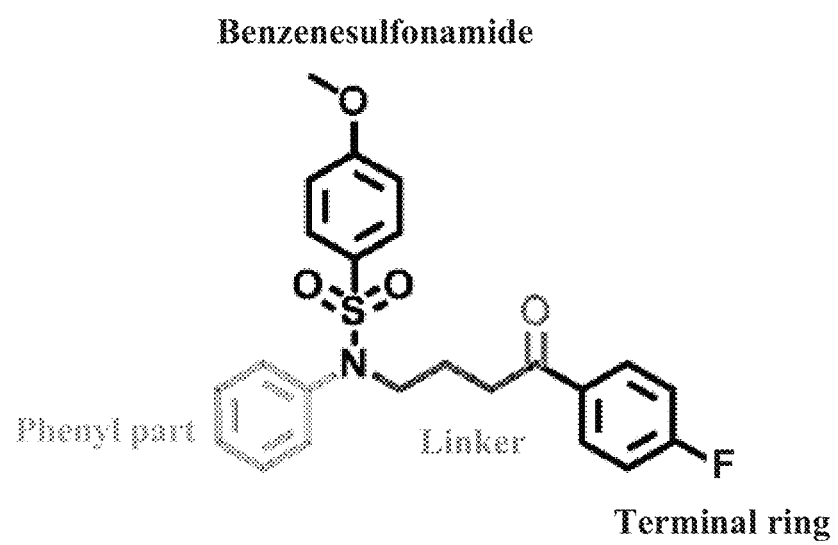
FIG. 1A shows the four substructures of the lead compound 1 that were assumed to affect the antiviral activity and cytotoxicity, including a phenyl part, a benzenesulfonamide part, a terminal ring, and a linker between the benzenesulfonamide part and the terminal ring.

Unless defined otherwise, all technical and scientific terms and abbreviations used herein have the same meaning as commonly understood by a person skilled in the art to which this invention pertains.

Definition

Numerical quantities given herein are approximate, and experimental values may vary within 20 percent, preferably within 10 percent, and most preferably within 5 percent. Thus, the terms "about" and "approximately" refer to within 20 percent, preferably within 10 percent, and most preferably within 5 percent of a given value or range.

Unless defined otherwise, the term "cycloalkyl" refers to a non-aromatic carbocyclic ring having 3 to 10 carbon ring atoms, which are carbon atoms bound together to form the ring. The ring may be saturated or have one or more carbon-carbon double bonds. Examples of cycloalkyl include, but not limited to cyclopropyl, cyclobutyl, cyclopentyl, cyclopentenyl, cyclohexyl, cyclohexenyl, and cycloheptyl, as well as bridged and caged saturated ring groups such as norbornyl and adamantyl.

The term "carbocycle" refers to a saturated carbocyclic, partially saturated carbocyclic, or aromatic ring system containing 3 to 14 carbon ring atoms. A carbocycle typically contains 3 to 10 carbon ring atoms, for example, cyclopropyl, cyclobutyl, cyclopentyl, cyclopentenyl, cyclopentadienyl, cyclohexyl, cyclohexenyl, cyclohexadienyl, and phenyl. A carbocycle alternatively may be two or three carbocyclic rings fused together, such as naphthalenyl, tetrahydronaphthalenyl, indenyl, isoindenyl, bicyclodecanyl, anthracenyl, phenanthrenyl, benzonaphthenyl (also known as phenalenyl), fluorenyl, and decalinyl.

The term "heterocycle" refers to a saturated cyclic, partially saturated cyclic, or aromatic ring system containing 3 to 14 ring atoms, in which at least one of the ring atom is a heteroatom that is oxygen, nitrogen, or sulfur. The heterocycle may be a monocyclic, bicyclic, or tricyclic ring system which may include fused rings. Examples of heterocycles include, but not limited to, azepine, pyrroles, thiophene, imidazole, furan, thiazole, isothiazole, isoxazole, indole, pyridine, pyridazine, pyrazine, piperidine, piperazine, tetrahydrofuran, tetrahydropyran, 1,4-dioxane, triazoles, tetrazole, benzimidazole, benzothiazole, benzopyrimidine, thiadiazole, purine, and quinolone.

Unless defined otherwise, the term "aryl" refers to a substituent containing one or two to three separate or fused rings, wherein at least one of the rings is 5- or 6-membered carbocyclic aromatic ring, such as benzene. The aryl substituent may have 6 to 18 carbon atoms. Examples of aryl substituent include phenyl, naphthyl, and anthracenyl. Examples of aryl substituent also include a $C_4$-$C_6$ carbocycle or a 4- to 6-membered heterocycle that is fused with phenyl, naphthyl, or anthracenyl, such as tetrahydronaphthalenyl, indenyl, isoindenyl, indanyl, phenanthrenyl, benzonaphthenyl, and fluorenyl. The aryl substituent may be substituted or unsubstituted. "Substituted" refers to a group in which one or more hydrogen atoms are each independently replaced with the same or different substituent(s). Typical substituents include, but are not limited to, —X, —$R^{1a}$, —$O^-$, =O, —$OR^{1a}$, —$SR^{1a}$, —$S^-$, =S, —$NR^{1a}R^{1b}$, =$NR^{1a}$, —$CX_3$, —$CF_3$, —CN, —OCN, —SCN, —NO, —$NO_2$, =$N_2$, —$N_3$, —$S(O)_2O^-$, —$S(O)_2OH$, —$S(O)_2R^{1a}$, —$OS(O)_2O^-$, —OS$(O)_2R^{1a}$, —$P(O)(O^-)_2$, —$P(O)(OR^{1a})(O^-)$, —$OP(O)(OR^{1a})$($OR^{1b}$), —$C(O)R^{1a}$, —$C(S)R^{1a}$, —$C(O)OR^{1a}$, —$C(O)NR^{1a}R^{1b}$, —$C(O)O^-$, —$C(S)OR^{1a}$, —$NR^{2a}C(O)NR^{1a}R^{1b}$, —$NR^{2a}C(S)NR^{1a}R^{1b}$, —$NR^{2a}C(NR^{1a})NR^{1a}R^{1b}$, —$C(NR^{1a})NR^{1a}R^{1b}$, —$S(O)_2NR^{1a}R^{1b}$, —$NR^{2a}S(O)_2R^{1a}$, —$NR^{2a}C(O)R^{1a}$, and —$S(O)R^{1a}$, where each X is independently a halogen; each $R^{1a}$ and $R^{1b}$ are independently hydrogen, alkyl, substituted alkyl, aryl, substituted aryl, arylalkyl, substituted arylalkyl, cycloalkyl, substituted cycloalkyl, cycloheteroalkyl, substituted cycloheteroalkyl, heteroaryl, substituted heteroaryl, heteroarylalkyl, substituted heteroarylalkyl, —$NR^{2a}R^{2b}$, —$C(O)R^{2a}$ or —$S(O)_2R^{2a}$; or optionally $R^{1a}$ and $R^{1b}$ together with the atom to which $R^{1a}$ and $R^{1b}$ are attached form one or more cycloheteroalkyl, substituted cycloheteroalkyl, heteroaryl, or substituted heteroaryl rings; and $R^{2a}$ and $R^{2b}$ are independently hydrogen, alkyl, substituted alkyl, aryl, substituted aryl, arylalkyl, substituted arylalkyl, cycloalkyl, substituted cycloalkyl, cycloheteroalkyl, substituted cycloheteroalkyl, heteroaryl, substituted heteroaryl, heteroarylalkyl or substituted heteroarylalkyl; or optionally $R^{2a}$ and $R^{2b}$ together with the nitrogen atom to which $R^{2a}$ and $R^{2b}$ are attached form one or more cycloheteroalkyl, substituted cycloheteroalkyl, heteroaryl, or substituted heteroaryl rings. In certain embodiments, a tertiary amine or aromatic nitrogen may be substituted with one or more oxygen atoms to form the corresponding nitrogen oxide.

The disclosed compounds may be administered to a subject in need by any suitable route, preferably in the form of a pharmaceutical composition adapted to such a route. For example, administration may be oral, transmucosal, or intestinal administration, or parenteral administration including intramuscular, subcutaneous, intrathecal, intraventricular, intravenous, intraperitoneal, intranasal, and intraocular injection.

The term "an effective amount" as used herein refers to the amount of an active ingredient that is required to confer therapeutic effects on the treated subject. Effective doses will vary, as recognized by those skilled in the art, depending on routes of administration, excipient usage, and the possibility of co-usage with other therapeutic treatment.

The term "pharmaceutically acceptable carrier" as used herein refers to any carrier that is compatible with the active ingredient of the composition (and preferably, capable of stabilizing the active ingredient) and not deleterious to the subject to be treated. Pharmaceutically acceptable carriers or excipients may include buffers such as phosphate, citrate, and other organic acids; antioxidants including ascorbic acid and methionine; preservatives such as octadecyldimethylbenzyl ammonium chloride, hexamethonium chloride, benzalkonium chloride, benzethonium chloride, phenol, benzyl alcohol, alkyl parabens such as methyl paraben, catechol, resorcinol, cyclohexanol, 3-pentanol, and m-cresol; low molecular weight (less than about 10 residues) polypeptides; amino acids such as glycine, glutamine, asparagine, histidine, arginine, or lysine; hydrophilic polymers such as polyvinylpyrrolidone; monosaccharides, disaccharides, and other carbohydrates including glucose, mannose, dextran, sucrose, mannitol, trehalose, and sorbitol; chelating agents such as ethylenediaminetetraacetic acid (EDTA); salt-forming counter-ions such as sodium; metal complexes such as Zn-protein complexes; and non-ionic surfactants such as TWEEN™ (polysorbate), PLURONICS™ (poloxamers), or polyethylene glycol (PEG).

The term "subject" refers to a mammal in need of treatment for diseases or conditions that are associated with CaMKII activity, for example, a flavivirus infection. The subject is human or non-human, such as a primate, mouse, dog, cat, cow, horse, rabbit, pig or the like.

Methods and Materials

Chemical Identification

All reagents and solvents were obtained from commercial sources and used as purchased unless otherwise stated. Tetrahydrofuran (THF) was freshly distilled from Na/benzophenone ketyl under an inert atmosphere of nitrogen. $^1$H nuclear magnetic resonance (NMR) and $^{13}$C NMR spectra were recorded on Bruker AVIII-400, AV-400 or AV-500. Proton chemical shifts were reported in parts per million (ppm) relative to the singlet at 7.24 ppm for the residual $CHCl_3$ in deuteriochloroform. Carbon chemical shifts were reported in parts per million relative to the internal $^{13}$C signals in $CDCl_3$ (77.0 ppm) and acetone-$d_6$ (29.1 ppm).

High resolution mass spectra (HRMS) were obtained with Waters LCT Premier XE (Waters Corp., Manchester, UK) and Bruker New ultrafleXtreme (Bruker, Bremen, Germany). Analytical thin layer chromatography (TLC) was performed on silica gel 60 $F_{254}$ (Merck). Column chromatography was performed with silica gel 60 (230-400 mesh) (Merck). The purity of compounds was established as >95% by normal phase high-performance liquid chromatography (HPLC) using Waters 1525 Binary System with a Waters 2489 dual λ absorbance detector, and Purospher STAR Si (5 µm) (Merck) and Venusil XBP Silica (Agela Technologies) columns. The eluent was ethyl acetate and hexane. All compounds were detected at 254 nm.

Cell Lines

All cells used in the examples were purchased from American Type Culture Collection (ATCC), including baby hamster kidney BHK-21 cells (ATCC CCL-10), mosquito C6/36 cells (ATCC CRL-1660), African green monkey kidney epithelial cells (Vero; ATCC CRL-1587), and human neuroblastoma BE(2)C cells (ATCC CRL-2268).

Construction of DENV-2-eGFP Reporter Virus

A DENV-2 infectious clone with the SP6 promoter (SP6-Den2) was established for evaluating the antiviral activity of candidate compounds. Briefly, genomic RNA of DENV-2 PL046 strain (GenBank accession number: AJ968413.1) was extracted and used for reverse transcription polymerase chain reaction (RT-PCR) to produce five cDNA fragments containing nucleotides 1-1512, 1342-4250, 4132-6375, 4522-9368, and 6838-10723, respectively. These cDNA fragments were cloned into the polylinker site of pJET1.2 vector. The full-length viral cDNA clone was then generated by standard restriction enzyme and ligation strategy by use of the pBR322 vector. To construct a DENV-2-eGFP reporter virus, a DNA fragment including eGFP cDNA and the porcine teschovirus (PTV1) 2A sequence was inserted into the SP6-Den2 between 5' UTR and DENV-2 ATG start codon. A silent mutation of the cyclization sequence (CS) of this SP6-Den2 was performed by single primer PCR mutagenesis. DNA sequences encoding the first 34 amino acids of DENV-2 capsid protein and containing the cyclization sequence were inserted into the SP6-Den2 infectious clone by PCR and blunt end ligation. The final clone contains the duplicated capsid element followed by eGFP-PTV2A and the 5' end of the DENV-2 genome with a conservatively mutated cyclization sequence (SP6-Den2 C34-eGFP-2A 5'CS mut). Viral RNA of this DENV-2 reporter virus was in vitro transcribed from the SP6 promoter. The DENV-2 reporter virus was produced by transfection of viral RNA into BHK-21 cells with Lipofectamine 2000 (Thermo Fisher Scientific). Amplification of the reporter virus was done in mosquito C6/36 cells.

Cell-Based Anti-DENV-2 Screening

Human neuroblastoma BE(2)C cells were cultured in RPMI 1640 medium (Gibco) supplemented with 10% fetal bovine serum (FBS). Before screening, BE(2)C cells were plated in a black 96-well plate with clear flat bottom (Corning Costar 3603). The cells were infected with the DENV-2-eGFP reporter virus at an MOI (multiplicity of infection) of 1 in the absence or presence of the indicated compound in various doses for 24 hours. Dimethyl sulfoxide (DMSO) was used as solvent control. The treated cells were fixed with 4% paraformaldehyde and stained with Hoechst for nuclei. The antiviral activity of candidate compounds was evaluated by measuring eGFP expression of the cell culture with ImageXpress Micro XLS High-Content Analysis System (Molecular Devices). The relative eGFP fluorescence intensity, indicating viral infection, was reported as a percentage of solvent control.

Cytotoxicity Assays

The cytotoxicity of candidate compounds to BE(2)C cells was evaluated by use of the cytotoxicity detection kit (LDH) (Roche), cell proliferation kit (XTT) (Roche), and Trypan blue cell counting assay. Briefly, cells were treated overnight with the candidate compounds at the indicated doses and subjected to the three assays. For LDH and XTT assays, light absorbance of the sample at 490 nm was determined by using an enzyme-linked immunosorbent assay (ELISA) reader (Molecular Devices). For Trypan blue cell counting assay, the number of viable cells was determined by use of haemocytometer. Data was normalized to solvent control and presented as a percentage.

Antiviral Assays

DENV-2 PL046 strain (GenBank accession number: AJ968413.1) isolated from a Taiwan dengue fever patient and ZIKV PRVABC59 strain (GenBank accession number: KU501215) provided by the Taiwan Centers for Disease Control were used for in vitro studies. BE(2)C cells were infected with DENV-2 or ZIKV at an MOI of 0.1 in the absence or presence of compound 9 in various doses for 48 hours. The antiviral activity of compound 9 was assessed by immunofluorescence assay (IFA), Western blotting, and plaque-forming assay (PFA). The expression of DENV-2 NS3 or ZIKV E protein was detected by incubating the cells with anti-DENV NS3 or anti-flavivirus E antibody, respectively. Alexa Fluor-488-conjugated anti-mouse secondary antibody (Molecular Probes) and Hoechst (Molecular Probes) for nuclei staining were used in IFA. The stained cells were examined under an inverted fluorescence microscope (Olympus 1X71). Anti-β-actin antibody (Chemicon) and horseradish peroxidase (HRP)-conjugated anti-mouse secondary antibody (Jackson ImmunoResearch) were used in Western blotting, and signals were detected by enhanced chemiluminescence (ECL; Pierce). The level of infectious DENV-2 and ZIKV particles was measured by PFA in BHK-21 and Vero cells, respectively. The virus titer was presented in Log plaque-forming unit (PFU)/mL and used to determine the half-maximal effective concentration ($EC_{50}$). The $EC_{50}$ was calculated by means of method known in the art. See, for example, Alexander, B. et al. A simple and accurate mathematical method for calculation of the EC50. *J Pharmacol Toxicol* 1999, 41, 55-58.

Virus Binding/Entry Assays

For virus binding/entry assay, BE(2)C cells were adsorbed with DENV-2 (MOI, 5) or ZIKV (MOI, 10) in the presence or absence of the indicated doses of compound 9 for 90 minutes with rocking at room temperature. For virus binding assay, BE(2)C cells were adsorbed with DENV-2 or ZIKV at 4° C. with rocking for 90 minutes in the absence or presence of compound 9. For the virus entry assay, BE(2)C cells were first adsorbed with DENV-2 or ZIKV at 4° C. for 90 minutes. Then, after a gentle wash with cold medium, the cells were incubated at 37° C. for 60 minutes in the absence or presence of compound 9 to allow virus entry. Thereafter, the cells were treated with an acidic glycine solution (0.1 M, pH=3) for 5 minutes to inactivate non-internalized virus and washed with cold Hank's balanced salt solution (HBSS). The cells were harvested with cell scrapers, and the adsorbed viruses were released by passing the cells through a 27-G needle 7 times. Cell lysates were centrifuged at 12,000 rpm for 1 minute, and the supernatant was used for plaque-forming assay to determine the level of virus binding and/or entry.

Animal Study

The mouse experiments were approved by the Academia Sinica Institutional Animal Care and Use Committee and performed in accordance with the guidelines. Infection was performed in mice under isoflurane anesthesia to minimize animal suffering. The DENV-2 New Guinea C strain serially passaged in mouse brain (NGC-N), kindly provided by Dr. Ching-Juh Lai (National Institutes of Health, USA) and ZIKV PRVABC59 strain were used in the animal study. Groups of 6-week-old Stat1$^{-/-}$ mice were intravenously infected in the tail with $1\times10^5$ PFU of DENV-2 per mouse or subcutaneously infected in the footpad with $5\times10^4$ PFU of ZIKV per mouse. To study the antiviral efficacy of compound 9, administered by an oral route, the mice were divided into several groups for various treatments: phosphate buffered saline (PBS; vehicle control); 2, 4, or 8 mg of compound 9/kg of body weight/day at the time of infection (immediate treatment); or 2, 4, or 8 mg of compound 9/kg of body weight/day at 8 hours post-infection (8-hours-delay treatment). Thereafter, the mice were administered daily with PBS or the same dose of compound 9 up to day 6 after infection. The mice were checked daily for severe symptoms including limb paralysis. Euthanasia of mice with severe limb paralysis was performed as the endpoint of animal survival. Mice survival was presented as percentage of survival. Mouse serum samples were collected on day 3 after infection by phlebotomy from facial vein, and the virus load was determined by plaque-forming assay.

Computational Docking Analysis

Molecular docking was performed by use of the online docking web server SwissDock and visualized by use of UCSF chimera to predict the interaction between ligand molecule and whole target protein. The X-ray crystal structure of human CaMKII, downloaded from Protein Data Bank (PDB entry: 2VZ6) and modified by removing Indirubin E804 and non-polar hydrogen atoms and adding polar hydrogen atoms, was used to model the drug target protein. Structure of compound 9, as the ligand molecule, was prepared by use of ChemSketch (ACD Inc).

CaMKII Biochemical Assay

The inhibitory effect of compounds 7, 8, 9, or 16 on purified human CaMKII (with the amino acid sequence of SEQ ID NO: 1) activity was measured by immunoassay that was performed according to the manufacturer's protocol (CycLex CaM kinase II Assay Kit, MBL Internationl Corp). The immunoassay is sensitive for semi-quantitative measurement of CaMKII activity that involves incubation of purified human CaMKII with a kinase substrate (syntide-2) in the presence of Ca$^{2+}$, calmodulin, Mg$^{2+}$, and ATP Briefly, kinase reaction buffers in the absence or presence of the indicated doses of compound 7, 8, 9, or 16 were loaded into a microtiter plate. A commercial CaMKII inhibitor, KN-62 (Selleckchem, S7422) was used as a positive control. Kinase reaction buffer without Ca$^{2+}$ was used as a negative control. The assay wells of the microtiter plate were then incubated with HRP-conjugated-anti-phospho-syntide-2 antibody, followed by addition of syntide-2. The phosphorylation reaction was stopped after incubation at room temperature for 15 minutes. Sample absorbance at 450 nm was determined by use of an ELISA reader (Molecular Devices). Data was normalized to solvent control and presented as a percentage.

Statistical Analysis

Data are presented as mean±standard deviation and were compared by ANOVA and Bonferroni post-hoc test unless otherwise specified. Statistical significance was set at P values of <0.05 or <0.01. A survival curve was descriptively analyzed by use of SigmaPlot v10.0 (Systat software). The median survival time (T$_{50}$) and P values, based on log-rank test, were determined by use of Prism v5.0 (GraphPad software). For Western blotting, the band intensity was quantified by use of ImageJ software (National Institutes of Health).

Example 1

Synthesis of Candidate Compounds 1-16

The procedure described below and shown in the following Schemes 1-3 exemplifies synthesis of certain compounds of the present invention. Starting from lead compound 1, which contains four substructures including a phenyl part, a benzenesulfonamide main part, a terminal ring, and a linker (FIG. 1A), four series of derivative compounds 2-16 (FIGS. 1B-1E) were prepared for studying the structure-antiviral activity relationship.

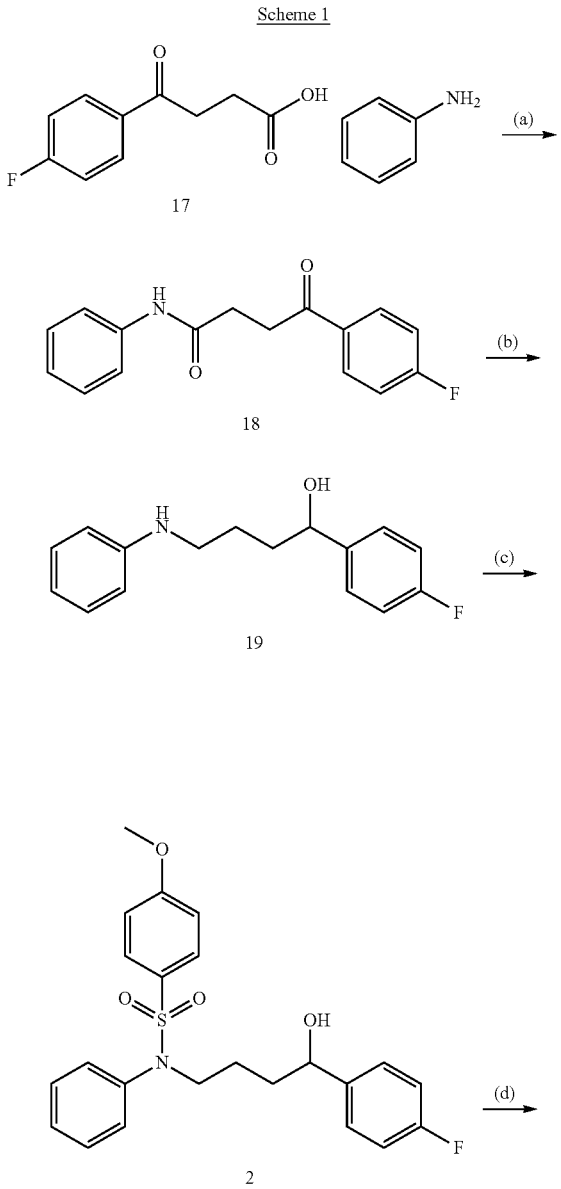

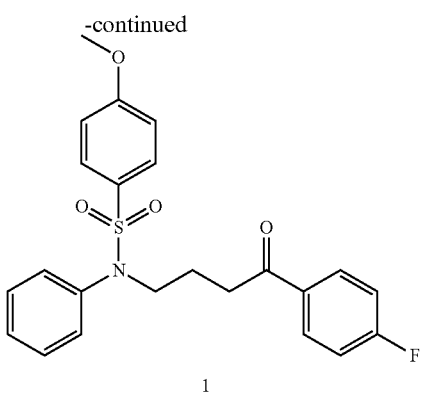

1

As shown in Scheme 1, the lead compound 1 and analog 2, bearing sulfonamide and fluorobenzene moieties, were initially prepared through condensation reaction of starting material acid 17 and aniline to form amide 18 via coupling reagents O-benzotriazol-1-yl-N,N,N',N'-tetramethyluroniumhexafluoro phosphate (HBTU) and diisopropylethylamine (DIPEA). After complete reduction by lithium aluminum hydride, the amine 19 was utilized to form sulfonamide 2 by reacting with 4-methoxybenzenesulfonyl chloride. Finally, the hydroxyl group of analog 2 was oxidized to ketone 1 by using pyridinium dichromate (PDC) in the presence of 4 Å molecular sieves, which enhanced reaction efficiency. The reagents and conditions for reactions indicated in Scheme 1 are summarized as follows: (a) HBTU, DIPEA, THF, 8 hours, room temperature (rt), 92%; (b) LiAlH$_4$, THF, 4 hours, 90° C., 90%; (c) 4-methoxybenzenesulfonyl chloride, Et$_3$N, THF, 60° C., 4 hours, 75%; (d) PDC, dichloromethane (DCM), 8 hours, rt, 70%.

Scheme 2

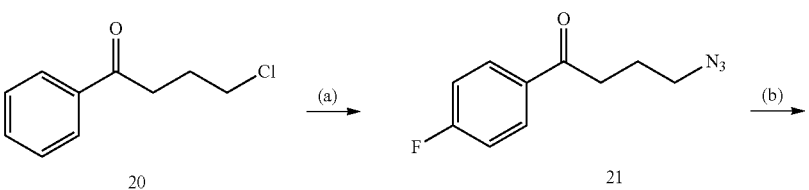

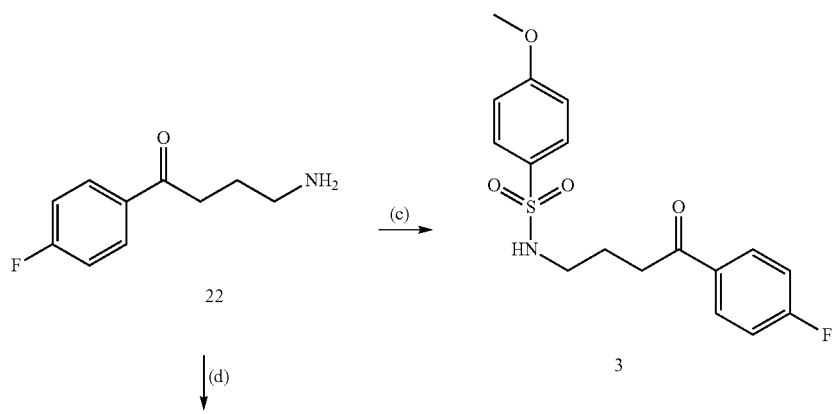

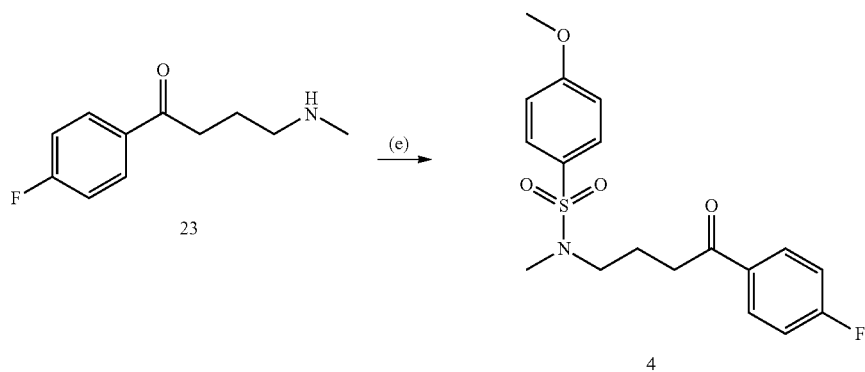

As shown in Scheme 2, the various substituted sulfonamides 3 and 4 were generated by introducing proton (H) and methyl ($CH_3$) groups at the N-substituent position of the 4-methoxybenzenesulfonamide to replace the original benzene ring. Conversion of chloride 20 to the corresponding amine 22 was accomplished in the presence of excess sodium azide and a catalytic amount of potassium iodide, followed by selective reduction by palladium on activated charcoal and hydrogen gas. Condensation of amine 22 and 4-methoxybenzenesulfonyl chloride furnished sulfonamide 3. The preparation of sulfonamide 4 began with imine formation from amine 22 using paraformaldehyde followed by selective reduction with sodium borohydride, and subsequent sulfonamide formation under the same condition. The reagents and conditions for reactions indicated in Scheme 2 are summarized as follows: (a) KI, $NaN_3$, dimethylformamide (DMF), 4 hours, 90° C.; (b) Pd/C, $H_2$, MeOH, 8 hours, rt; (c) 4-methoxybenzenesulfonyl chloride, $Et_3N$, THF, 60° C., 4 hours, 48%; (d) (1) HCHO, NaOMe, MeOH, 90° C., 4 hours, (2) $NaBH_4$, MeOH, rt, 4 hours, 63%; (e) 4-methoxybenzenesulfonyl chloride, $Et_3N$, THF 60° C., 4 hours, 78%.

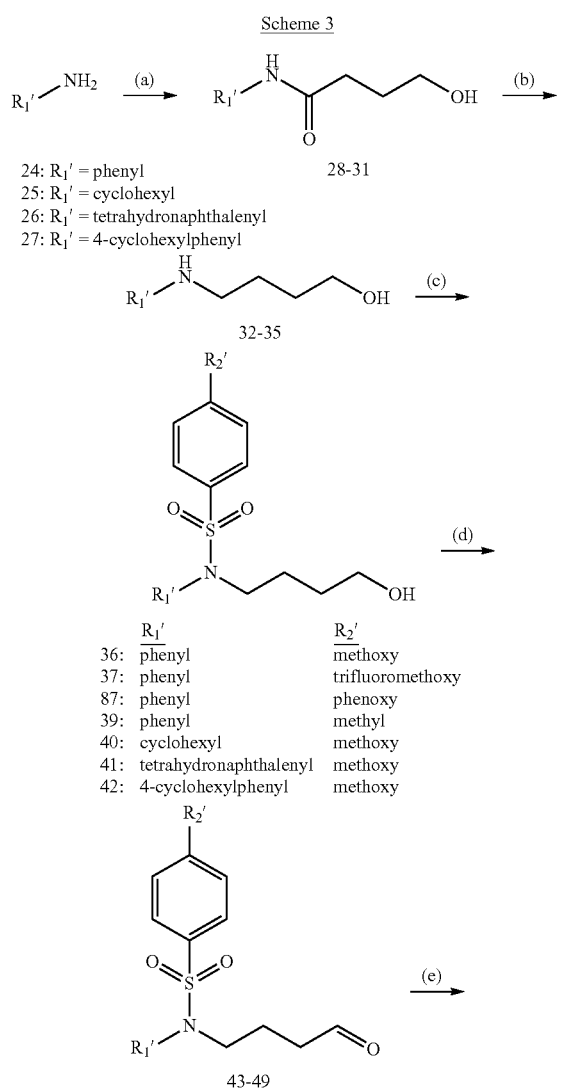

Scheme 3

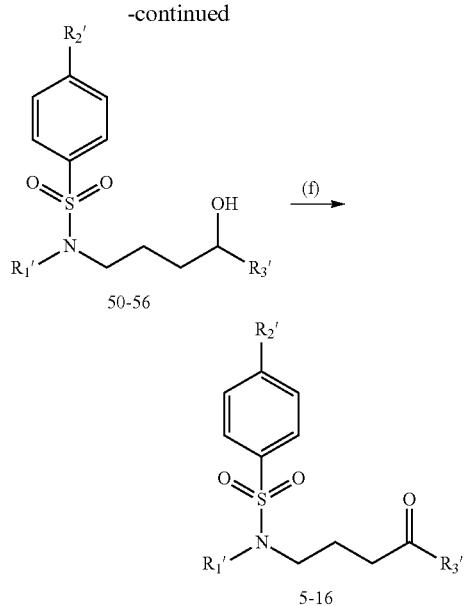

As shown in Scheme 3, benzenesulfonamide analogs 5-16, derived from modifications of the phenyl, the terminal ring, the linker, and the benzenesulfonamide part of the lead compound, were synthesized. Aminolysis of γ-butyrolactone by the corresponding amine 24-27 in the presence of sodium hydride at 90° C. gave carboxamides 28-31, which were reduced by $LiAlH_4$ to yield secondary amines 32-35. Furthermore, condensation of differently substituted benzenesulfonyl chlorides and amines 32-35 followed by mild oxidation in the present of pyridinium dichromate afforded aldehydes 43-49, respectively. The addition of an excess of a Grignard reagent to the corresponding aldehydes 43-49 gave secondary alcohols 50-56, which were further oxidized by a solution of pyridinium dichromate to obtain the respective target compounds 5-16, whose $R_1'$, $R_2'$, and $R_3'$ groups are shown in TABLE 1. The reagents and conditions for reactions indicated in Scheme 3 are summarized as follows: (a) (1) NaH, THF, 30 minutes, 90° C., (2) butyrolactone, THF, 8 hours, 90° C., 90%; (b) $LiAlH_4$, THF, 8 hours, 90° C.; (c) substituted benzenesulfonyl chloride, $Et_3N$, THF, 60° C., 4 hours, 76%; (d) PDC, DCM, 8 hours, rt, 65%; (e) (1) $R_2Br$, Mg, THF, 2 hours, rt, (2) aldehyde, THF, 60° C., 2 hours, 60%; (f) PDC, DCM, 8 hours, rt.

TABLE 1

| Compound | $R_1'$ | $R_2'$ | $R_3'$ |
|---|---|---|---|
| 5 | phenyl | methoxy | methyl |
| 6 | phenyl | methoxy | cyclohexyl |
| 7 | phenyl | methoxy | cyclobutyl |
| 8 | phenyl | methoxy | cyclopentyl |
| 9 | phenyl | methoxy | cycloheptyl |
| 10 | phenyl | methoxy | adamantyl |
| 11 | phenyl | trifluoromethoxy | cyclopentyl |
| 12 | phenyl | phenoxy | cycloheptyl |
| 13 | phenyl | methyl | cycloheptyl |
| 14 | cyclohexyl | methoxy | cycloheptyl |
| 15 | tetrahydronaphthalenyl | methoxy | cycloheptyl |
| 16 | 4-cyclohexylphenyl | methoxy | cycloheptyl |

The preparation methods of candidate compounds 1-16 are detailed as follows.

1.1 Preparation of Compound 2, N-(4-(4-fluorophenyl)-4-hydroxybutyl)-4-methoxy-N-phenylbenzenesulfonamide

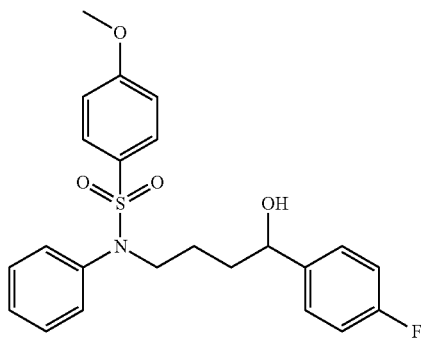

2

A solution of aniline (2 mL, 21.93 mmol), acid 17 (4.30 g, 21.93 mmol), HBTU (9.15 g, 24.12 mmol), and DIPEA (7.64 mL, 43.86 mmol) in THF (60 mL) were stirred at room temperature for 8 hours. The reaction mixture was dried under reduced pressure and purified by column chromatography to obtain amide 18 as a white solid (5.47 g, 92%). Lithium aluminum hydride (696 mg, 18.40 mmol) was suspended in dry in THF (100 mL) under argon at room temperature. A solution of amide 18 (2 g, 7.36 mmol) in THF (10 mL) was added dropwise over 30 minutes at 0° C. under argon. Next, the reaction mixture was stirred at 90° C. for 8 hours, and then was extracted with ethyl acetate and water, dried over magnesium sulfate, and concentrated in vacuum. Amine 19 was obtained as a gray oil (1.72 g, 90%), which was directly used in next step without further purification. A solution of 4-methoxybenzenesulfonyl chloride (1.59 g, 7.71 mmol), triethylamine (2.15 mL, 15.42 mmol), and amine 19 (2 g, 7.71 mmol) in THF (60 mL) was stirred at 60° C. for 8 hours. The reaction mixture was extracted with ethyl acetate and water. The combined organic layer were dried by magnesium sulfate and concentrated in vacuum. The residue was subjected to flash column chromatography, followed by normal-phase HPLC to afford the pure product 2 as a colorless oil (2.48 g, 75%). $^1$H NMR (400 MHz, CDCl$_3$) δ 1.42-1.54 (m, 2H), 1.78-1.84 (m, 2H), 3.55-3.60 (m, 2H), 3.88 (s, 3H), 4.68 (t, J=6.4 Hz, 2H), 6.91 (d, J=8.4 Hz, 2H), 7.01-7.04 (m, 4H), 7.26-7.31 (m, 5H), 7.50 (d, J=8.4 Hz, 2H); $^{13}$C NMR (100 MHz, acetone-d$_6$) δ 24.3, 36.3, 50.0, 55.3, 71.9, 114.0, 114.5, 114.7, 127.6, 127.6, 128.8, 128.8, 129.7, 130.3, 139.5, 142.1, 161.8 (d, J=251 Hz). HRMS (ESI) calculated for C$_{23}$H$_{24}$NO$_4$FS (M+Na)$^+$, 452.1308; found, 452.1301.

1.2 Preparation of Compound 1, N-(4-(4-fluorophenyl)-4-oxobutyl)-4-methoxy-N-phenylbenzenesulfonamide

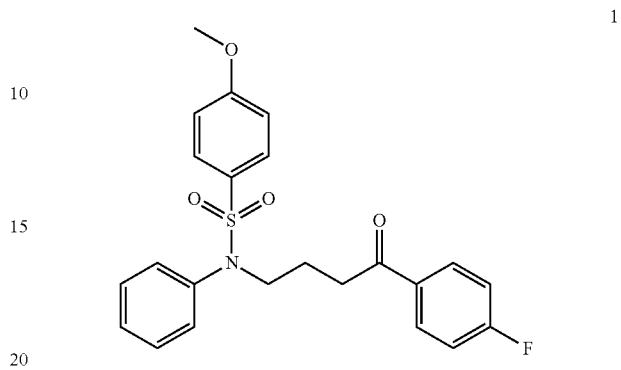

1

A solution of pyridinium dichromate (0.91 g, 2.43 mmol) and compound 2 (0.8 g, 1.87 mmol) in the presence of 4 Å molecular sieves (1.0 g) in DCM (30 mL) was stirred at room temperature for 8 hours. The reaction mixture was extracted with ethyl acetate and water. The combined organic layers were dried over magnesium sulfate and concentrated in vacuum. The residue was subjected to flash column chromatography, followed by normal-phase HPLC to afford the pure compound 1 as a white solid (70%): mp 93-94° C. $^1$H NMR (400 MHz, CDCl$_3$) δ 1.82-1.89 (m, 2H), 3.09-3.12 (t, J=7.0 Hz, 2H), 3.66-3.69 (t, J=6.2 Hz, 2H), 3.87 (s, 3H), 6.91 (d, J=8.4 Hz, 2H), 7.08-7.15 (m, 4H), 7.31-7.33 (m, 3H), 7.51 (d, J=8.0 Hz, 2H), 7.96-7.99 (m, 2H); $^{13}$C NMR (125 MHz, CDCl$_3$) δ 22.3, 35.0, 49.6, 55.6, 55.75, 114.0, 115.6 (d, J=22 Hz), 128.0, 128.7, 129.1, 129.7, 130.6, 130.7, 133.3, 139.0, 162.9, 165.7 (d, J=253 Hz), 197.7. HRMS (ESI) calculated for C$_{23}$H$_{22}$NO$_4$FS (M+Na)$^+$, 450.1151; found, 450.1146.

1.3 Preparation of Compound 3, N-(4-(4-fluorophenyl)-4-oxobutyl)benzenesulfonamide

3

A solution of sodium azide (1.06 g, 16.24 mmol), chloride 20 (1.3 mL, 8.12 mmol), and potassium iodide (134 mg, 0.81 mmol) in DMF (30 mL) was stirred at 90° C. for 8 hours. The reaction mixture was extracted with ethyl acetate and water. The combined organic layers were dried over magnesium sulfate and concentrated in vacuum. The crude residue 21 was used without further purification. A solution of residue 21 (2 g, 9.65 mmol) and palladium on active charcoal (0.21 g, 0.97 mmol) in MeOH (10 mL) was stirred at room temperature under hydrogen gas (1 bar) for 8 hours. The reaction mixture was filtered to obtain amine 22. A mixture of 4-methoxybenzenesulfonyl chloride (2.19 g, 10.62 mmol) and triethylamine (2.94 mL, 21.12 mmol) was added to a solution of the amine 22 (dissolve in MeOH from previous step) in dry THF (50 mL) and the mixture was stirred at 60° C. for 8 hours. The reaction mixture was extracted with ethyl acetate and water then dried over magnesium sulfate, and concentrated in vacuum. The residue was subjected to flash column chromatography, followed by normal-phase HPLC to afford the pure compound 3 as a white solid (48%): mp 84-85° C. $^1$H NMR (400 MHz, acetone-$d_6$) δ 1.85-1.92 (m, 2H), 3.00-3.03 (m, 2H), 3.05-3.10 (m, 2H), 3.88 (s, 3H), 6.39 (t, J=5.6 Hz, 1H), 7.08 (d, J=8.8 Hz, 2H), 7.24-7.28 (m, 2H), 7.80 (d, J=8.8 Hz, 2H), 8.02-8.06 (m, 2H); $^{13}$C NMR (100 MHz, acetone-$d_6$) δ 23.1, 34.9, 42.4, 55.2, 114.1, 115.4 (d, J=22 Hz), 128.9, 130.7 (d, J=9 Hz), 132.8, 133.7, 162.7, 165.5 (d, J=250 Hz), 197.3. HRMS (ESI) calculated for $C_{17}H_{18}NO_4FS$ (M+Na)$^+$, 374.0838; found, 374.0843.

1.4 Preparation of Compound 4, N-(4-(4-fluorophenyl)-4-oxobutyl)-4-methoxy-N-methylbenzenesulfonamide

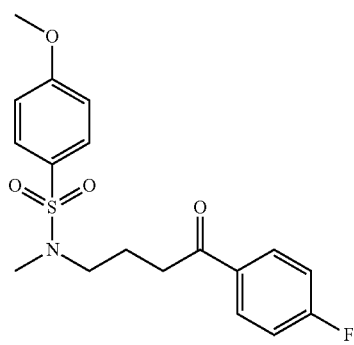

A solution of paraformaldehyde (0.23 g, 7.64 mmol), amine 22 (1 g, 5.46 mmol), and sodium methoxide (1.47 g, 27.30 mmol) in MeOH (30 mL) was stirred at 90° C. for 4 hours, and then the reaction mixture was cooled to room temperature. Sodium borohydride (0.41 g, 10.92 mmol) was slowly added into the reaction mixture over 5 minutes. The reaction mixture was extracted with ethyl acetate and water, then dried over magnesium sulfate, concentrated in vacuum, and purified by flash column chromatography to give compound 23 (0.67 g, 63%). A solution of 4-methoxybenzenesulfonyl chloride (1.05 g, 5.12 mmol), triethylamine (1.43 mL, 10.24 mmol), and compound 23 (1.0 g, 5.12 mmol) in THF (20 mL) was stirred at 60° C. for 8 hours. The reaction mixture was extracted with ethyl acetate and water then dried over magnesium sulfate, and concentrated in vacuum. The residue was subjected to flash column chromatography, followed by normal-phase HPLC to afford the pure compound 4 as a white solid (1.46 g, 78%): mp 89-90° C. $^1$H NMR (500 MHz, CDCl$_3$) δ 1.90-1.96 (m, 2H), 2.67 (s, 3H), 3.01-3.05 (m, 4H), 3.81 (s, 3H), 6.91-6.94 (m, 2H), 7.06-7.10 (m, 2H), 7.64-7.67 (m, 2H), 7.93-7.97 (m, 2H); $^{13}$C NMR (125 MHz, CDCl$_3$) δ 21.5, 34.7, 35.0, 49.4, 55.6, 114.2, 115.7 (d, J=22 Hz), 129.0, 129.4, 130.7 (d, J=9 Hz), 133.3, 162.8, 164.7 (d, J=254 Hz), 197.9. HRMS (ESI) calculated for $C_{18}H_{20}FNO_4S$ (M+Na)$^+$, 388.0995; found, 388.0995.

1.5 General Procedures for Preparation of Candidate Compounds 5-16

Amine 24 (5 mL, 54.76 mmol) was added dropwise to a mixture of sodium hydride (2.52 g, 65.71 mmol) and THF (100 mL) over 30 minutes. The reaction mixture was stirred at 90° C. for 1 hour, followed by dropwise addition of butyrolactone (4.17 mL, 54.76 mmol) over 10 minutes. After 8 hours, the reaction mixture was extracted with ethyl acetate and water then dried over magnesium sulfate, and concentrated in vacuum. The residue was subjected to flash column chromatography to give amide 28 (8.83 g, 90%) as a white solid.

The amide 28 (4.0 g, 22.35 mmol) in THF (50 mL) was added dropwise to a mixture of lithium aluminum hydride (2.12 g, 55.84 mmol) and THF (100 mL) over 30 minutes at 0° C. under argon. The reaction mixture was stirred at 90° C. for 8 hours, and then extracted with ethyl acetate and water, dried over magnesium sulfate, and concentrated in vacuum. The secondary amine 32 was obtained, which was directly used in next step without further purification.

A solution of 4-methoxybenzenesulfonyl chloride (4.94 g, 23.99 mmol), triethylamine (5.57 mL, 39.98 mmol), and alcohol 32 (3.30 g, 19.99 mmol) in THF (60 mL) was stirred at 60° C. for 4 hours. The reaction mixture was extracted with ethyl acetate and water then dried over magnesium sulfate, and concentrated in vacuum. The residue was subjected to flash column chromatography to give sulfonyl amide 36 (5.09 g, 76%).

A mixture of 4 Å molecular sieves (3.00 g) and pyridinium dichromate (5.09 g, 13.47 mmol) was added to a solution of sulfonyl amide 36 (3.00 g, 8.98 mmol) in DCM. The mixture was stirred for 8 hours at room temperature, and then extracted with ethyl acetate and water, dried over magnesium sulfate, and concentrated in vacuum. The residue was subjected to flash column chromatography to afford aldehyde 43 (1.95 g, 65%) as a colorless solid.

A solution of methyl iodide (0.42 mL, 6.75 mmol) and magnesium (131 mg, 5.40 mmol) in THF (10 mL) was stirred at 60° C. for 1 hour, and then the mixture was cooled to room temperature. Aldehyde 43 (0.45 g, 1.36 mmol) in THF (10 mL) was added dropwise over 10 minutes. After 2 hours, the reaction mixture was extracted with ethyl acetate and water, dried over magnesium sulfate, and concentrated in vacuum. The secondary alcohol 50 was obtained, which was directly used in next step without further purification.

A mixture of 4 Å molecular sieves (1.00 g) and pyridinium dichromate (764 mg, 2.03 mmol) was added to a solution of alcohol 50 in dry DCM (30 mL). The mixture was stirred for 8 hours at room temperature, and then extracted by ethyl acetate and water, dried over magnesium sulfate, and concentrated in vacuum. The residue was subjected to flash column chromatography, followed by normal-phase HPLC to afford the pure compound 5 (0.28 g, 60%).

1.5.1

4-methoxy-N-(4-oxopentyl)-N-phenylbenzenesulfonamide (5)

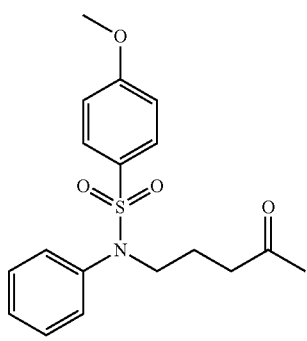

A white solid; yield 33%; mp 81-82° C. $^1$H NMR (500 MHz, CDCl$_3$) δ 1.60-1.62 (m, 2H), 2.08 (s, 3H), 2.54 (t, J=7 Hz, 2H), 3.49 (t, J=6.5 Hz, 2H), 3.807 (s, 3H), 6.85-6.86 (m, 2H), 6.99 (d, J=7 Hz, 2H), 7.24-7.26 (m, 3H), 7.44 (d, J=7 Hz, 2H); $^{13}$C NMR (125 MHz, CDCl$_3$) δ 21.8, 30.1, 39.8, 49.5, 55.6, 113.9, 127.9, 128.7, 129.1, 129.7, 139.0, 162.9, 208.1. HRMS (ESI) calculated for C$_{18}$H$_{21}$NO$_4$S (M+Na)$^+$, 370.1089; found, 370.1084.

1.5.2

N-(4-cyclohexyl-4-oxobutyl)-4-methoxy-N-phenyl-benzenesulfonamide (6)

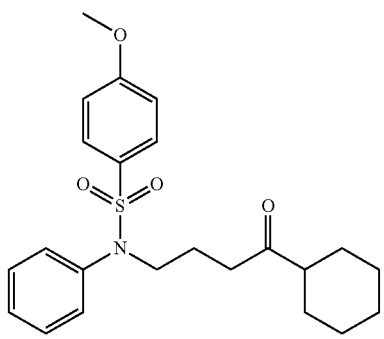

A white solid; yield 32%; mp 81-82° C. $^1$H NMR (500 MHz, CDCl$_3$) δ 1.30-1.35 (m, 4H), 1.66-1.68 (m, 4H), 1.70-1.86 (m, 4H), 2.35 (m, 1H), 2.61 (t, J=7 Hz, 2H), 3.57 (t, J=7 Hz, 2H), 3.90 (s, 3H), 6.94 (d, J=8.5 Hz, 2H), 7.07-7.09 (m, 2H), 7.32-7.35 (m, 3H), 7.52 (d, J=8.5 Hz, 2H); $^{13}$C NMR (125 MHz, CDCl$_3$) δ 21.8, 25.7, 25.7, 25.8, 28.5, 28.5, 36.8, 49.6, 50.8, 55.6, 113.9, 127.9, 128.7, 129.0, 129.7, 129.8, 139.0, 162.9. HRMS (ESI) calculated for C$_{23}$H$_{29}$NO$_4$S (M+Na)$^+$, 438.1715; found, 438.1710.

1.5.3

N-(4-cyclobutyl-4-oxobutyl)-4-methoxy-N-phenyl-benzenesulfonamide (7)

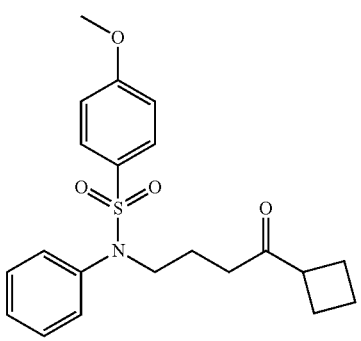

A gray viscous liquid; yield 32%. $^1$H NMR (400 MHz, CDCl$_3$) δ 1.61-1.67 (m, 2H), 1.73-1.80 (m, 1H), 1.89-1.98 (m, 1H), 2.05-2.21 (m, 4H), 2.45 (t, J=6.8 Hz, 2H), 3.16-3.23 (m, 1H), 3.51 (t, J=6.8 Hz, 2H), 3.83 (s, 3H), 6.86-6.99 (m, 2H), 7.00-7.02 (d, J=8 Hz, 2H), 7.26-7.28 (m, 3H), 7.45 (d, J=8 Hz, 2H); $^{13}$C NMR (100 MHz, CDCl$_3$) δ 17.9, 22.0, 24.6, 24.6, 36.3, 45.7, 49.8, 55.8, 114.1, 128.1, 128.9, 129.2, 130.0, 130.1, 139.2, 163.1, 211.3. HRMS (ESI) calculated for C$_{21}$H$_{25}$NO$_4$S (M+Na)$^+$, 410.1402; found, 410.1407.

1.5.4

N-(4-cyclopentyl-4-oxobutyl)-4-methoxy-N-phenyl-benzenesulfonamide (8)

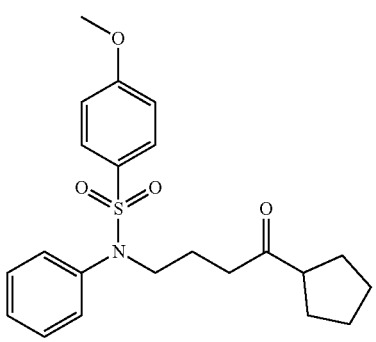

A white solid; yield 35%; mp 89-90° C. $^1$H NMR (400 MHz, CDCl$_3$) δ 1.57-1.78 (m, 10H), 2.53 (t, J=7 Hz, 2H), 2.75-2.83 (m, 1H), 3.50 (t, J=6.4 Hz, 2H), 3.80 (s, 3H), 6.84-6.87 (m, 2H), 6.98-7.01 (m, 2H), 7.22-7.26 (m, 3H), 7.43 (d, J=8.8 Hz, 2H); $^{13}$C NMR (100 MHz, CDCl$_3$) δ 22.2, 26.1, 26.1, 29.1, 29.1, 38.1, 49.8, 51.7, 55.7, 114.1, 128.1, 128.9, 129.0, 129.2, 129.9, 139.2, 163.0, 212.7. HRMS (ESI) calculated for C$_{22}$H$_{27}$NO$_4$S (M+Na)$^+$, 424.1559; found, 424.1552.

1.5.5

N-(4-cycloheptyl-4-oxobutyl)-4-methoxy-N-phenyl-benzenesulfonamide (9)

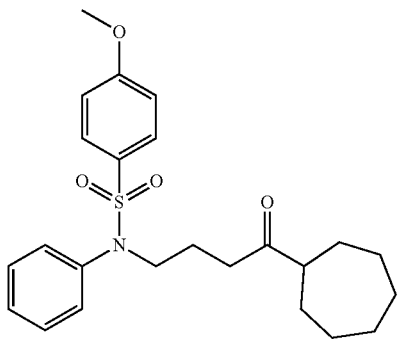

A white solid; yield 34%; mp 75-76° C. $^1$H NMR (400 MHz, CDCl$_3$) δ 1.62-1.71 (m, 6H), 1.75-1.80 (m, 8H), 2.44-2.50 (m, 1H), 2.55 (t, J=7.2 Hz, 2H), 3.51 (m, J=6.4 Hz, 2H), 3.83 (s, 3H), 6.87 (d, J=8.8 Hz, 2H), 7.01-7.03 (m, 2H), 7.27-7.28 (m, 3H), 7.45 (d, J=8.8 Hz, 2H); $^{13}$C NMR (100 Hz, CDCl$_3$) δ 22.2, 26.9, 26.9, 28.5, 28.5, 30.1, 30.1, 37.2, 49.8, 52.6, 55.8, 114.1, 128.1, 128.9, 129.2, 130.0, 139.3, 163.1, 213.9. HRMS (ESI) calculated for C$_{24}$H$_{31}$NO$_4$S (M+Na)$^+$, 452.1872; found, 452.1866.

1.5.6

N-(4-(adamantan-2-yl)-4-oxobutyl)-4-methoxy-N-phenylbenzenesulfonamide (10)

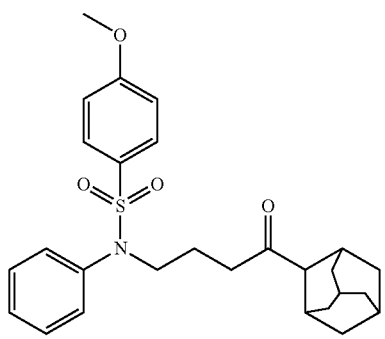

A white solid; yield 35%; mp 117-118° C. $^1$H NMR (400 MHz, CDCl$_3$) δ 1.54-1.88 (m, 14H), 2.29-2.31 (m, 2H), 2.41-2.42 (m, 1H), 2.53 (t, J=7.2 Hz, 2H), 3.52 (t, J=6.4 Hz, 2H), 3.83 (s, 3H), 6.89 (d, J=7.2 Hz, 2H), 7.00-7.02 (m, 2H), 7.26-7.28 (m, 3H), 7.45 (d, J=9.2 Hz, 2H); $^{13}$C NMR (100 Hz, CDCl$_3$) δ 22.2, 27.7, 27.8, 29.4, 29.4, 33.5, 33.5, 36.2, 37.5, 38.5, 38.5, 49.8, 55.8, 57.3, 114.1, 128.1, 128.9, 129.2, 129.9, 139.2, 163.0, 212.3. HRMS (ESI) calculated for C$_{27}$H$_{33}$NO$_4$S (M+Na)$^+$, 490.2028; found, 490.2033.

1.5.7

N-(4-cyclopentyl-4-oxobutyl)-N-phenyl-4-(trifluoromethoxy)benzenesulfonamide (11)

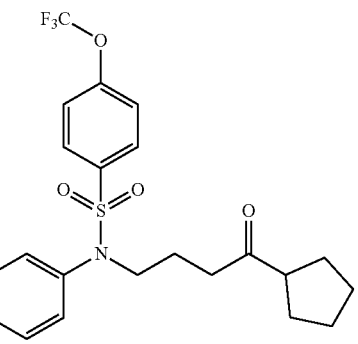

A white solid; yield 32%; mp 69-70° C. $^1$H NMR (400 MHz, CDCl$_3$) δ 1.56-1.77 (m, 8H), 1.79-1.82 (m, 2H), 2.56 (t, J=7.2 Hz, 2H), 2.78-2.86 (m, 1H), 3.56 (t, J=6.4 Hz, 2H), 7.00-7.03 (m, 2H), 7.23-7.25 (m, 2H), 7.29-7.31 (m, 3H), 7.57-7.59 (m, 2H); $^{13}$C NMR (100 Hz, CDCl$_3$) δ 22.1, 26.2, 26.2, 28.1, 28.1, 39.0, 50.0, 51.7, 120.7, 128.2, 128.8, 129.5, 130.0, 136.6, 138.6, 152.3, 212.6. HRMS (ESI) calculated for C$_{22}$H$_{25}$NO$_4$SF$_3$ (M+H)$^+$, 456.1456; found, 456.1458.

1.5.8

N-(4-cycloheptyl-4-oxobutyl)-4-phenoxy-N-phenyl-benzenesulfonamide (12)

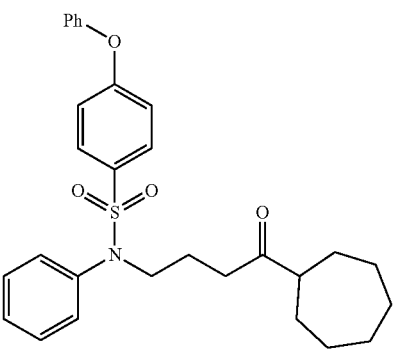

A white solid; yield 35%; mp 127-128° C. $^1$H NMR (400 MHz, CDCl$_3$) δ 1.40-1.80 (m, 14H), 2.45-2.49 (m, 1H), 2.55 (t, J=7.2 Hz, 2H), 3.53 (t, J=6.4 Hz, 2H), 6.93-6.95 (m, 2H), 7.03-7.05 (m, 4H), 7.18-7.30 (m, 4H), 7.37-7.41 (m, 2H), 7.46-7.48 (m, 2H); $^{13}$C NMR (100 Hz, CDCl$_3$) δ 22.3, 26.9, 26.9, 28.5, 28.5, 30.2, 30.2, 37.2, 49.9, 52.7, 117.5, 120.5, 125.1, 128.2, 128.9, 129.3, 130.1, 130.4, 132.0, 139.1, 155.4, 161.7, 213.9. HRMS (ESI) calculated for C$_{29}$H$_{33}$NO$_4$S (M+Na)$^+$, 514.2028; found, 514.2023.

1.5.9

N-(4-cycloheptyl-4-oxobutyl)-4-methyl-N-phenyl-benzenesulfonamide (13)

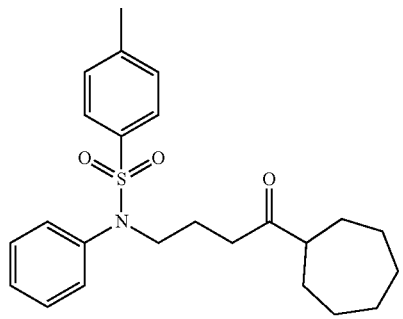

A gray viscous liquid; yield 23%. $^1$H NMR (300 MHz, CDCl$_3$) δ 1.46-1.91 (m, 16H), 2.46 (s, 3H), 2.50-2.57 (m, 1H), 2.62 (t, J=7.2 Hz, 2H), 3.58 (t, J=6.6 Hz, 2H), 7.06-7.09 (m, 2H), 7.26-7.35 (m, 5H), 7.47 (d, J=8.4 Hz, 2H); $^{13}$C NMR (75 Hz, CDCl$_3$) δ 21.7, 22.2, 26.7, 26.7, 28.5, 28.5, 30.2, 30.2, 37.2, 49.9, 52.7, 127.9, 128.1, 129.0, 129.3, 129.6, 135.4, 139.2, 143.6, 214.0. HRMS (ESI) calculated for C$_{24}$H$_{31}$NO$_3$S (M+Na)$^+$, 436.1922; found, 436.1917.

1.5.10

N-(4-cycloheptyl-4-oxobutyl)-N-cyclohexyl-4-methoxybenzenesulfonamide (14)

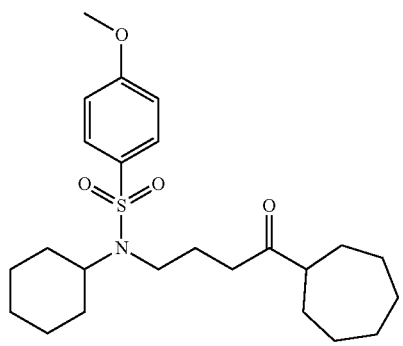

A gray viscous liquid; yield 32%. $^1$H NMR (400 MHz, CDCl$_3$) δ 1.28-1.86 (m, 23H), 2.49 (t, J=7.2 Hz, 2H), 3.07-3.11 (m, 2H), 3.50-3.56 (m, 1H), 3.82 (s, 3H), 6.96 (d, J=8, 2H), 7.69-7.71 (m, 2H); $^{13}$C NMR (100 MHz, CDCl$_3$) δ 25.5, 26.0, 26.3, 26.3, 26.9, 26.9, 28.5, 28.5, 30.2, 30.2, 31.9, 31.9, 37.9, 43.3, 52.5, 55.7, 58.2, 114.3, 129.1, 162.7, 214.2. HRMS (ESI) calculated for C$_{24}$H$_{25}$NO$_4$S (M+Na)$^+$, 446.1402; found, 446.1402.

1.5.11

N-(4-cycloheptyl-4-oxobutyl)-4-methoxy-N-(5,6,7,8-tetrahydronaphthalen-2-yl)-benzenesulfonamide (15)

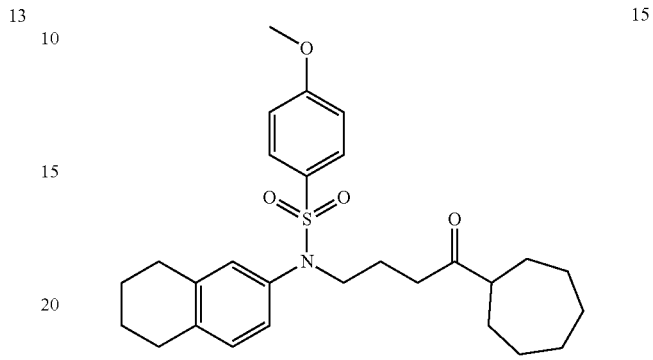

A white solid; yield 32%; mp 111-112° C. $^1$H NMR (300 MHz, CDCl$_3$) δ 1.47-1.78 (m, 18H), 2.50-2.55 (m, 3H), 2.76-2.79 (m, 3H), 2.95-3.08 (m, 1H), 3.17-3.24 (m, 1H), 3.60-3.70 (m, 1H), 3.87 (s, 3H), 6.38-6.41 (m, 1H), 6.92-7.04 (m, 4H), 7.60 (d, J=9 Hz, 2H); $^{13}$C NMR (75 MHz, CDCl$_3$) δ 22.5, 22.8, 22.9, 26.0, 26.0, 26.9, 26.9, 28.5, 29.9, 30.1, 30.2, 37.8, 51.5, 52.6, 55.8, 114.1, 125.2, 125.6, 129.5, 130.3, 130.8, 138.4, 139.5, 139.6, 163.1, 213.7. HRMS (ESI) calculated for C$_{28}$H$_{37}$NO$_4$S (M+Na)$^+$, 506.2341; found, 506.2322.

1.5.12

N-(4-cycloheptyl-4-oxobutyl)-N-(4-cyclohexylphenyl)-4-methoxybenzenesulfonamide (16)

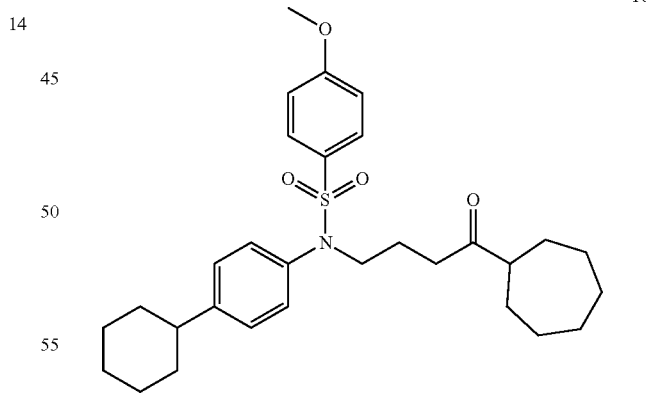

A white solid; yield 35%; mp 103-104° C. $^1$H NMR (300 MHz, CDCl$_3$) δ 1.32-1.82 (m, 24H), 2.47-2.48 (m, 2H), 2.55 (t, J=7.2 Hz, 2H), 3.47 (t, J=6.6 Hz, 2H), 3.83 (s, 3H), 6.86-6.92 (m, 4H), 7.09 (d, J=8.4 Hz, 2H), 7.47 (d, J=8.7 Hz, 2H); $^{13}$C NMR (75 MHz, CDCl$_3$) 22.2, 26.2, 26.8, 26.8, 26.9, 26.9, 28.4, 28.4, 30.1, 30.1, 34.5, 34.5, 37.2, 44.2, 49.9, 52.5, 55.7, 114.0, 127.5, 128.3, 129.9, 130.2, 136.7, 148.0, 162.9, 214.0. HRMS (ESI) calculated for C$_{30}$H$_{41}$NO$_4$S (M+Na)$^+$, 534.2654; found, 534.2648.

Example 2

Structure-Activity Relationship (SAR) Screening

For preliminary antiviral screening of the candidate compounds 1-16 described in Example 1, a DENV-2 reporter virus that expresses an enhanced-green fluorescence protein (termed DENV-2-eGFP) was used to infect human neuronal BE(2)C cells in the absence or presence of the indicated compounds. TABLE 2 shows the relative eGFP fluorescence intensity of cells treated with 3.125 µM of the indicated compound. In addition, the effect of 6.25 µM of the indicated compound on cell proliferation was evaluated by use of XTT assay.

TABLE 2

| Compound | DENV-2 infection % | Cell proliferation % |
|---|---|---|
| 1 | 39.3 | 56.1 |
| 2 | 48.5 | 76.3 |
| 3 | 122.6 | 105.7 |
| 4 | 100.9 | 105.9 |
| 5 | 100.8 | 105.9 |
| 6 | 63.3 | 106.6 |
| 7 | 33.0 | 93.9 |
| 8 | 25.1 | 90.0 |
| 9 | 9.6 | 90.0 |
| 10 | 51.1 | 96.7 |
| 11 | 118.2 | 92.4 |
| 12 | 73.4 | 95.5 |
| 13 | 76.9 | 99.5 |
| 14 | 65.7 | 97.5 |
| 15 | 21.5 | 103.6 |
| 16 | 13.8 | 100.4 |

Figure 1B:
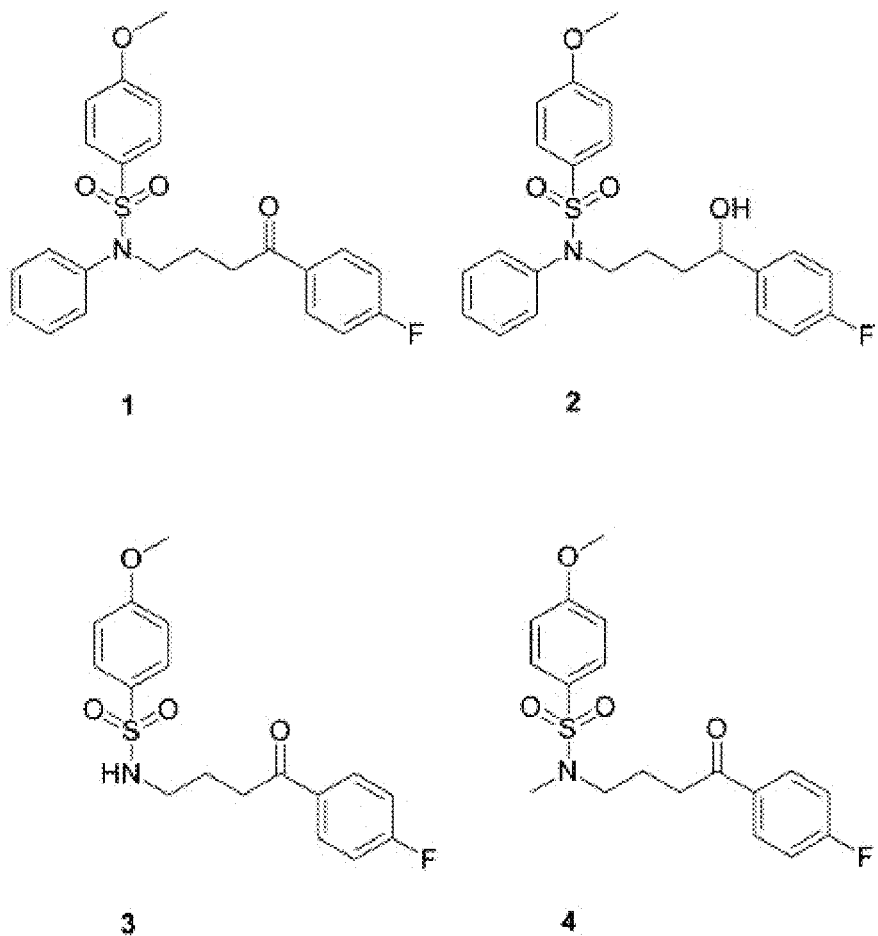
FIG. 1B shows the chemical structures of compounds 1-4, which are structurally different at the ketone in the linker and the phenyl part.

According to TABLE 2, treatment with the lead compound 1 resulted in 39.3% infection of DENV-2 in BE(2)C cells and reduced cell proliferation to 56.1% compared to solvent control. The first series of compounds are structurally different at the ketone in the linker and the phenyl part (FIG. 1B). The reduction of the ketone group of compound 1 to the hydroxyl group of compound 2 yielded 48.5% infection and improved cell proliferation to 76.3%. When the phenyl group of compound 1 was substituted with hydrogen or methyl group in compound 3 and 4, respectively, no cytotoxicity of the compounds was observed, however, these substitutions caused loss of antiviral potency against DENV-2, leading to 122.6% (compound 3) or 100.9% (compound 4) infection. These data indicate that a benzene ring is required for the anti-DENV activity of the benzenesulfonamide derivatives.

Figure 1C:
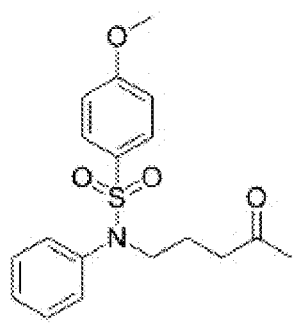
FIG. 1C shows the chemical structures of compounds 5-10, which are structurally different at the terminal ring.
Figure 1C:
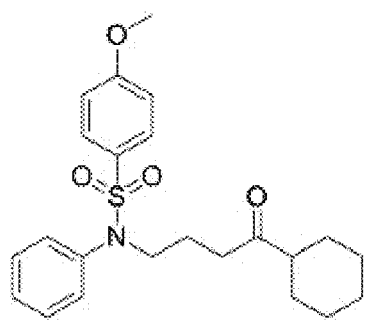
Figure 1C:
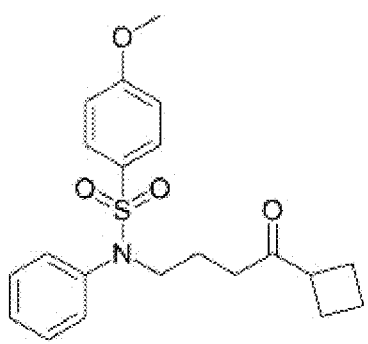
Figure 1C:
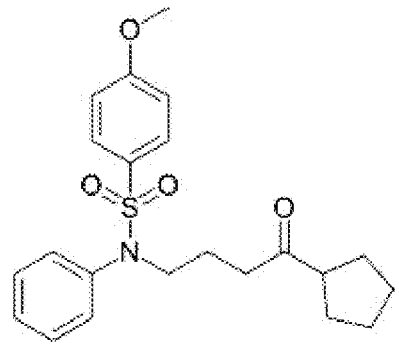
Figure 1C:
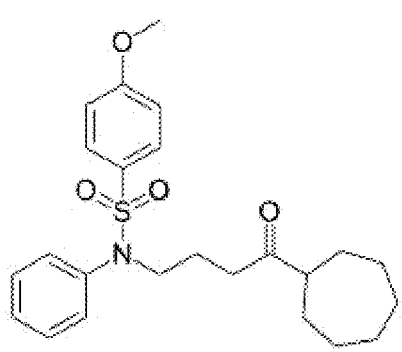
Figure 1C:
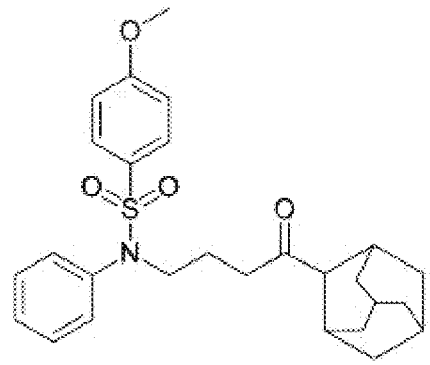
Figure 1D:
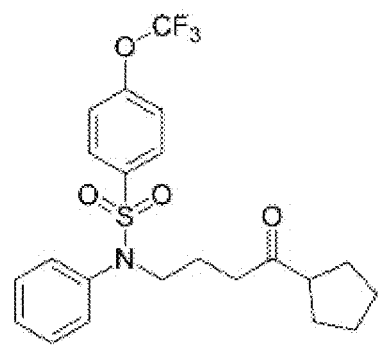
FIG. 1D shows the chemical structures of compounds 11-13, which are structurally different at the benzenesulfonamide part.
Figure 1D:
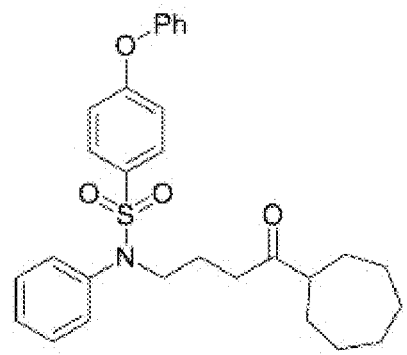
Figure 1D:
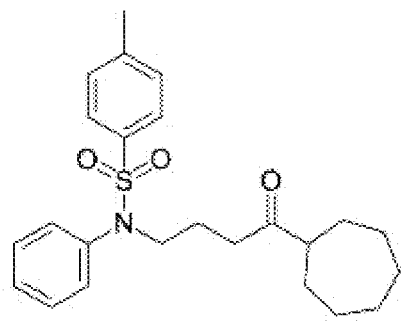

Building on these observations, the second series of compounds were generated that are structurally different at the terminal ring of the linker (FIG. 1C). Treatment with compound 5, having a methyl substitution, displayed no observable anti-DENV effect (100.8% infection). Compound 6 with a cyclohexyl substitution regained the antiviral activity (63.3% infection), although the antiviral potency was less than compound 1. Substitution with cyclobutyl or cyclopentyl at the terminal ring in compounds 7 and 8 resulted in 33% and 25.1% infection, respectively, indicating a comparable antiviral activity with compound 1. Notably, the cytotoxicity of compound 7 or 8 was greatly reduced as compared with compound 1. Cycloheptyl substitution in compound 9 resulted in a remarkable reduction in DENV-2 infection to 9.6% with minor effect on cell proliferation. Substituted with adamantyl, compound 10 yielded 51.1% DENV-2 infection and minor effect on cell proliferation.

In the third series of compounds (FIG. 1D), the methoxy group of the benzenesulfonamide was modified to trifluoromethyl (compound 11), phenoxy (compound 12), or methyl (compound 13). Treatment with compound 11, 12, or 13 resulted in 118.2%, 73.4%, and 76.9% DENV-2 infection, respectively. Minor effect on cell proliferation was observed in the cells treated with these compounds. The results indicate that methoxy group of the substituted benzenesulfonamides is critical for the antiviral activity.

Figure 1E:
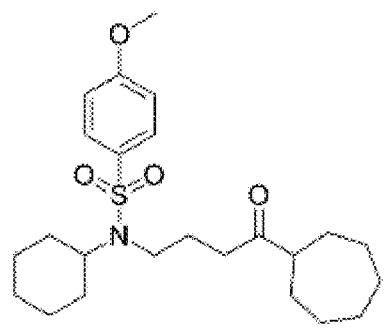
FIG. 1E shows the chemical structures of compounds 14-16, which are structurally different at the phenyl part.
Figure 1E:
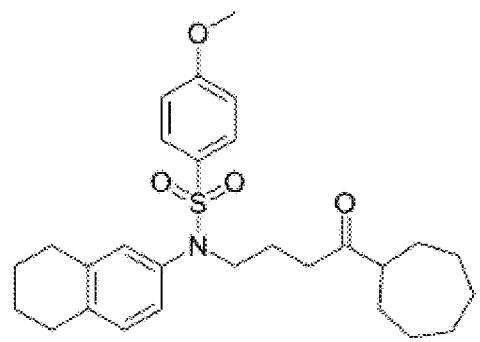
Figure 1E:
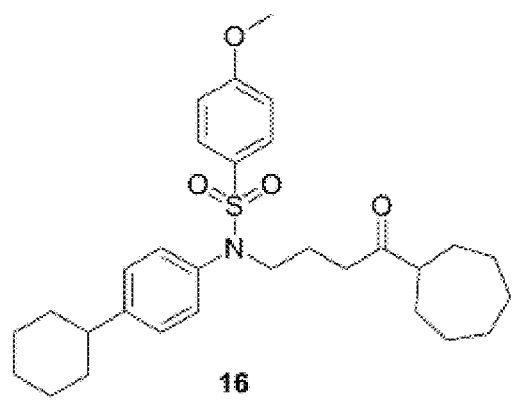

In addition, the phenyl group of the compound 9 was changed into aliphatic ring (compound 14). We observed minor cell toxicity and 65.7% DENV-2 infection in the cells treated with compound 14. Furthermore, to increase the compound solubility, the phenyl group was extended into tetrahydronaphthalenyl (compound 15) or 4-cyclohexylphenyl (compound 16) (FIG. 1E). Treatment with compound 15 or 16 resulted in 21.5% and 13.8% DENV-2 infection, respectively, with no effect on proliferation of BE(2)C cells.

Taken together, the anti-DENV activity of the lead compound 1 requires substructures including a phenyl part, a ketone in the linker, and a methoxybenzenesulfonamide. Moreover, aliphatic substitutions at the terminal ring greatly increase the antiviral potency and reduce the cytotoxicity of lead compound 1, and extra rings linked to the phenyl part may increase solubility.

Example 3

Compound 9 Inhibits DENV-2 and ZIKV Infection In Vitro

According to Example 2, compound 9 displays the most favorable antiviral activity with a tolerable cytotoxic effect as compared with the other benzenesulfonamide derivatives. Therefore, the antiviral potency of compound 9 against wild type DENV-2 and ZIKV infections was further studied. Firstly, the non-cytotoxic doses of compound 9 were determined comprehensively with three different assays: the LDH cytotoxicity assay, the XTT cell proliferation assay, and Trypan blue cell counting assay. Thereafter, antiviral assay was performed with BE(2)C cells infected with DENV-2 (MOI, 0.1) or ZIKV (MOI, 0.1) in the absence or presence of non-cytotoxic compound 9 and assayed for viral protein expression and viral progeny production.

Figure 2A:
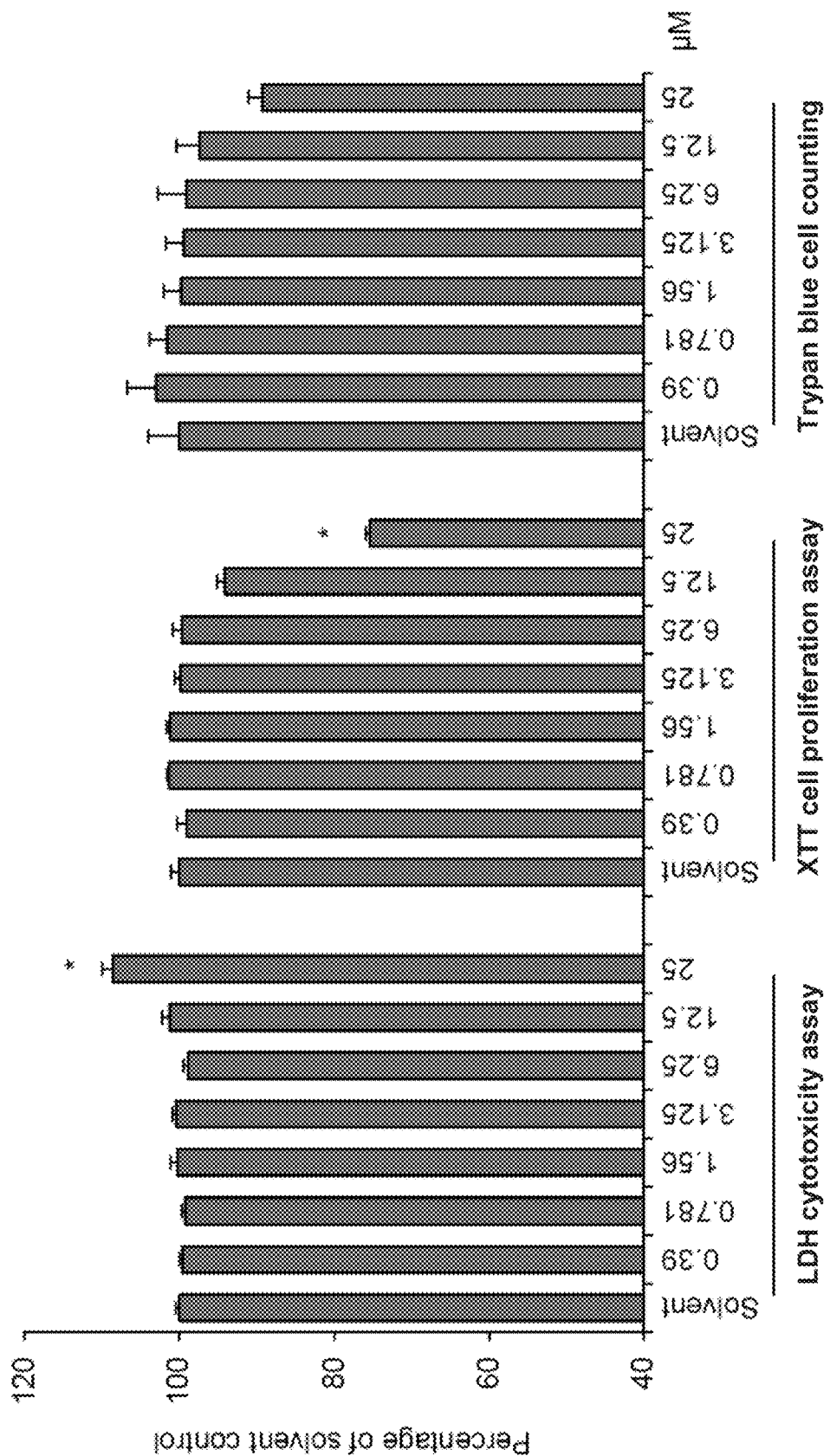
FIG. 2A shows the cytotoxic effect of various doses of compound 9 on BE(2)C cells, which were treated with compound 9 at the indicated doses and subjected to LDH cytotoxicity, XTT cell proliferation, and Trypan blue cell counting assays; * indicates $P<0.05$ based on student T-test compared with solvent control.

As shown FIG. 2A, compound 9, up to 12.5 µM, had no significant cytotoxicity and had no significant effect on the proliferation and viability of BE(2)C cells.

Figure 2B:
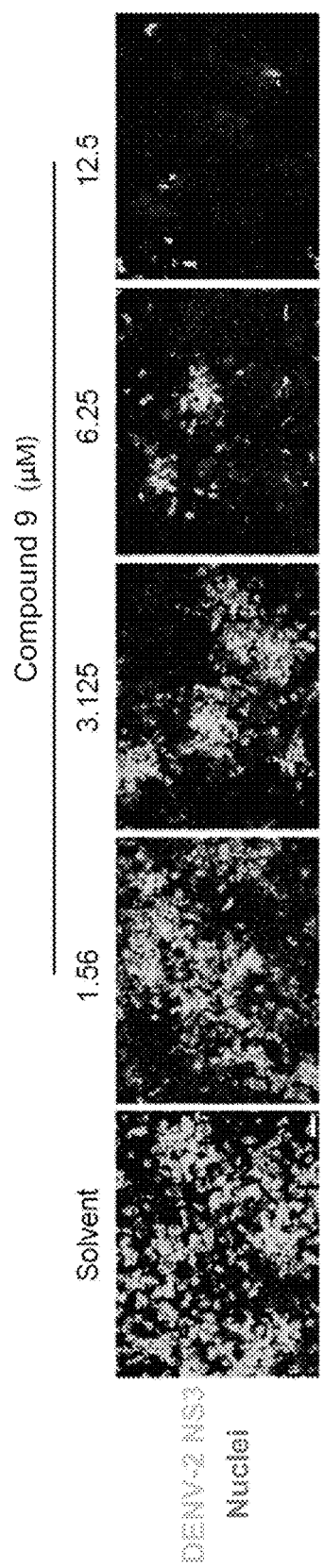
FIG. 2B shows immunofluorescence images of BE(2)C cells infected with type 2 dengue virus (DENV-2) in the absence or presence of compound 9 at the indicated doses and immunostained for DENV-2 NS3 protein and nuclei.
Figure 2C:
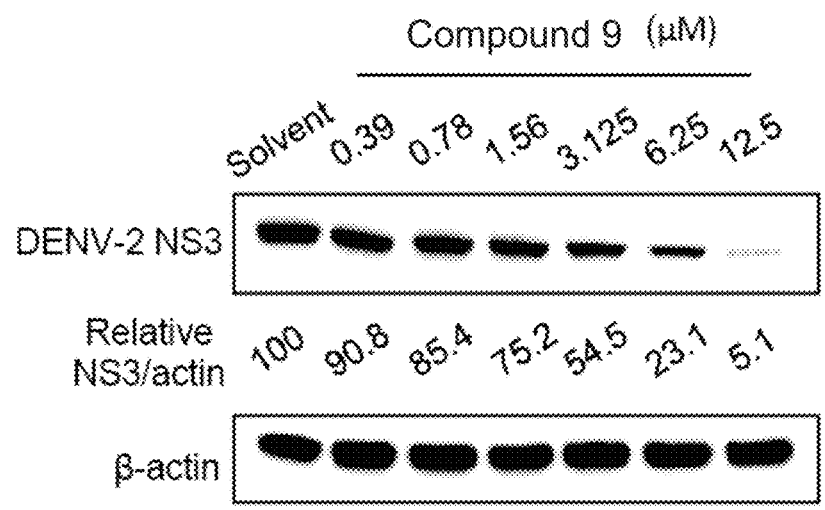
FIG. 2C shows Western blot analysis of protein levels of DENV-2 NS3 and β-actin (as loading control) in the cells of FIG. 2B; relative ratios of NS3 protein to actin are normalized to solvent control.
Figure 2D:
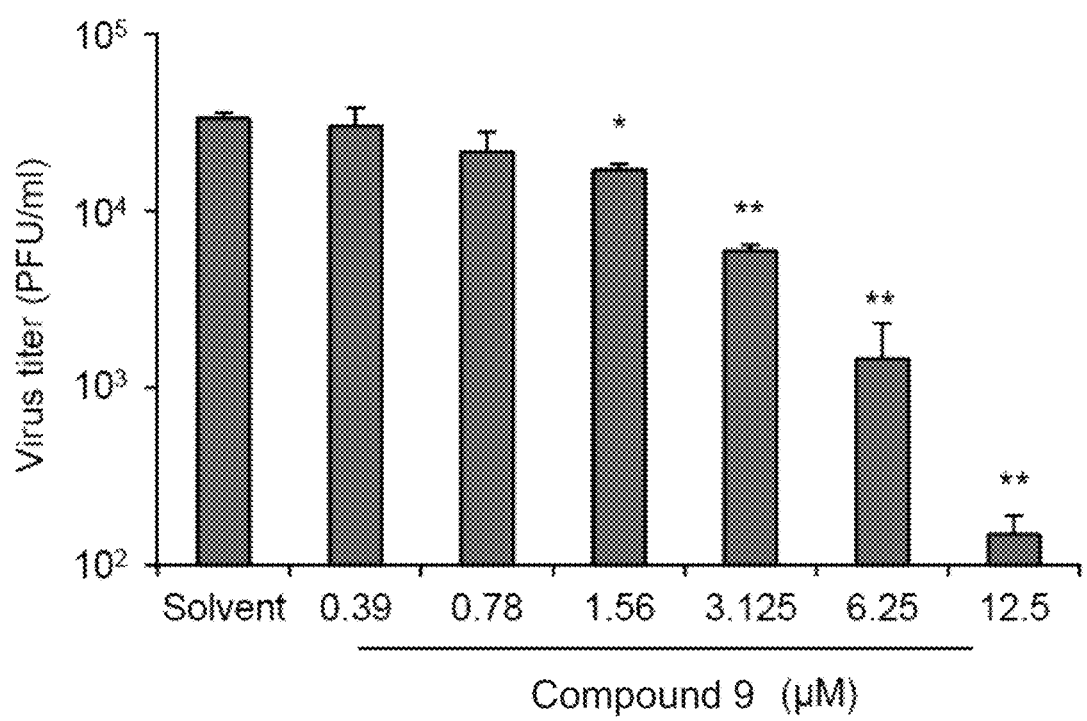
FIG. 2D shows virus titers of the culture supernatants of the cells of FIG. 2B; * and ** indicate $P<0.05$ and $P<0.01$, respectively, based on student T-test compared with solvent control.
Figure 2E:
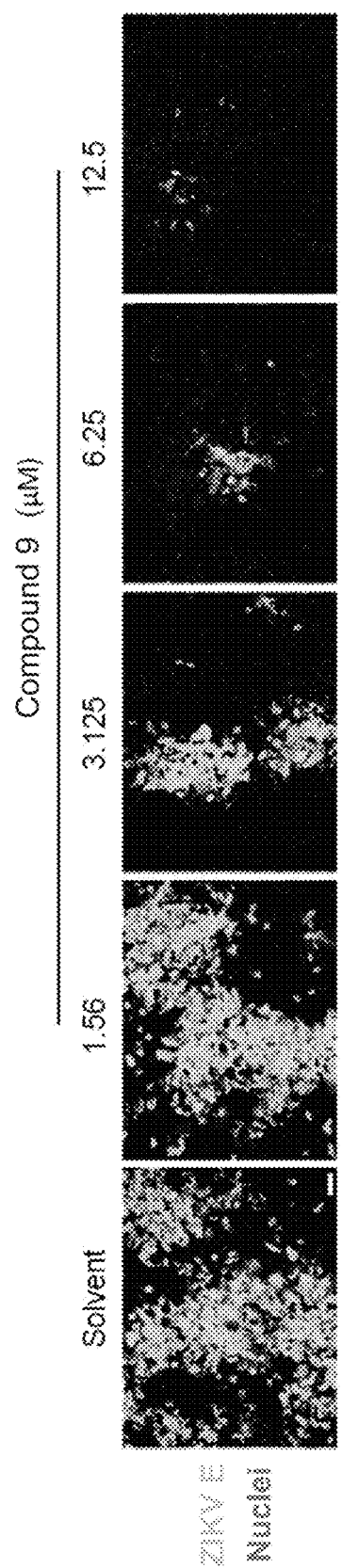
FIG. 2E shows immunofluorescence images of BE(2)C cells infected with ZIKV in the absence or presence of compound 9 at the indicated doses for 48 hours and immunostained for ZIKV E protein and nuclei.
Figure 2F:
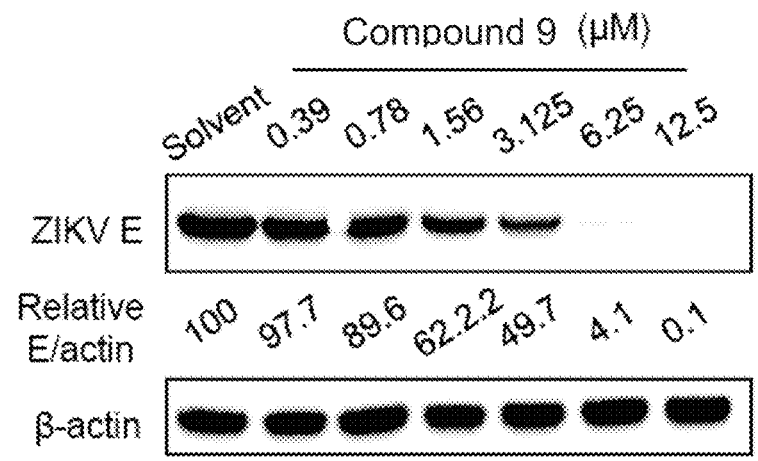
FIG. 2F shows Western blot analysis of protein levels of ZIKV E and β-actin (as loading control) in the cells of FIG. 2E; relative ratios of E protein to actin are normalized to solvent control.
Figure 2G:
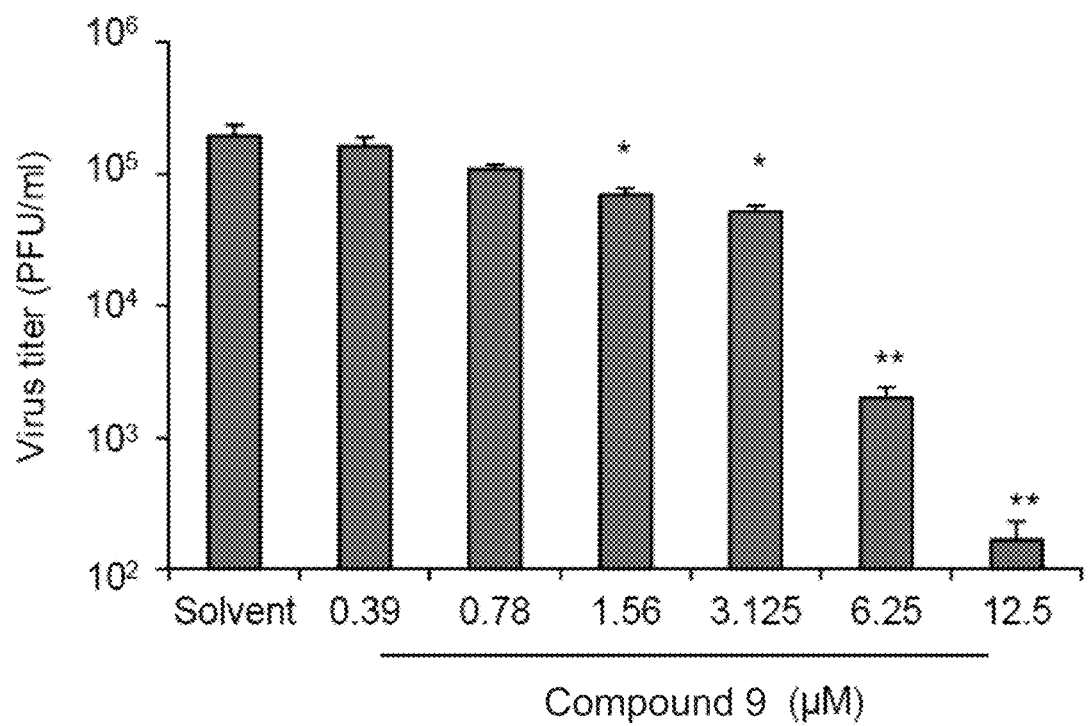
FIG. 2G shows virus titers of the culture supernatants of the cells of FIG. 2E; * and ** indicate $P<0.05$ and $P<0.01$, respectively, based on student T-test compared with solvent control.

According to FIGS. 2B-2D, treatment with non-cytotoxic compound 9 significantly reduced DENV-2 NS3 protein expression and viral progeny production in a dose-dependent manner, with an $EC_{50}$ of 1.52 µM. Similarly, as shown in FIGS. 2E-2G, treatment with non-cytotoxic compound 9 significantly inhibited ZIKV E protein expression and viral progeny production, with an $EC_{50}$ of 1.91 µM. Thus, at non-cytotoxic concentrations, compound 9 showed antiviral effects against wild type DENV-2 and ZIKV infections.

Example 4

Compound 9 Blocks the Viral Entry of DENV-2 and ZIKV

Figure 3A:
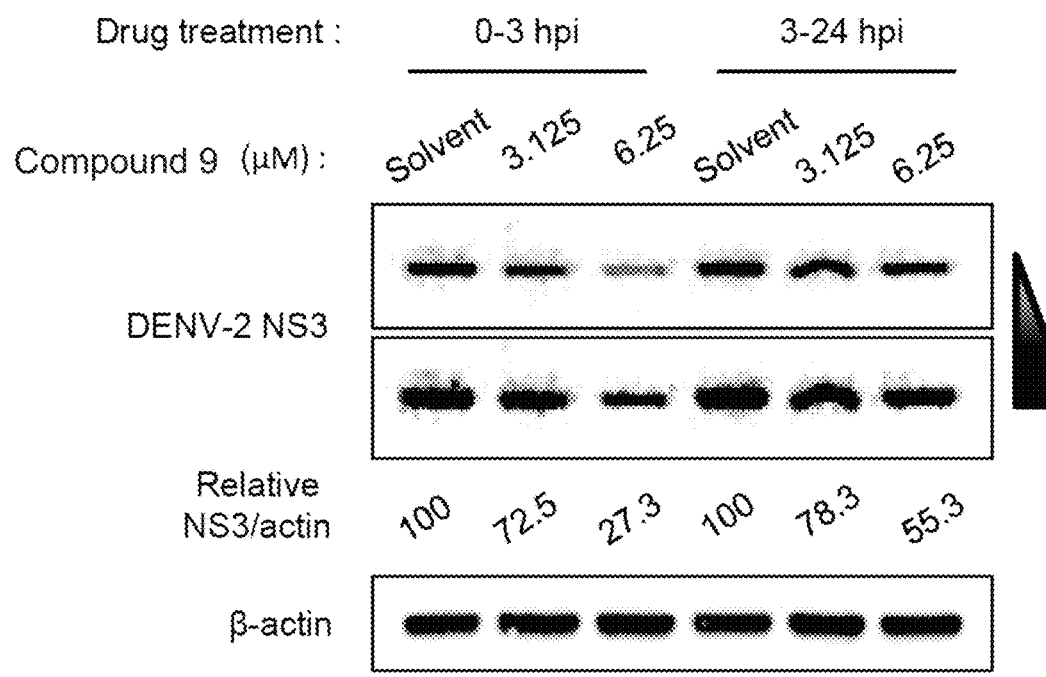
FIG. 3A shows Western blot analysis of protein levels of DENV-2 NS3 and β-actin (as loading control) in the BE(2)C cells infected with DENV-2 in the absence or presence of compound 9 at the indicated doses during (0-3 hours post infection (hpi)) or after (3-24 hpi) virus adsorption; relative ratios of NS3 protein to actin are normalized to solvent control.
Figure 3B:
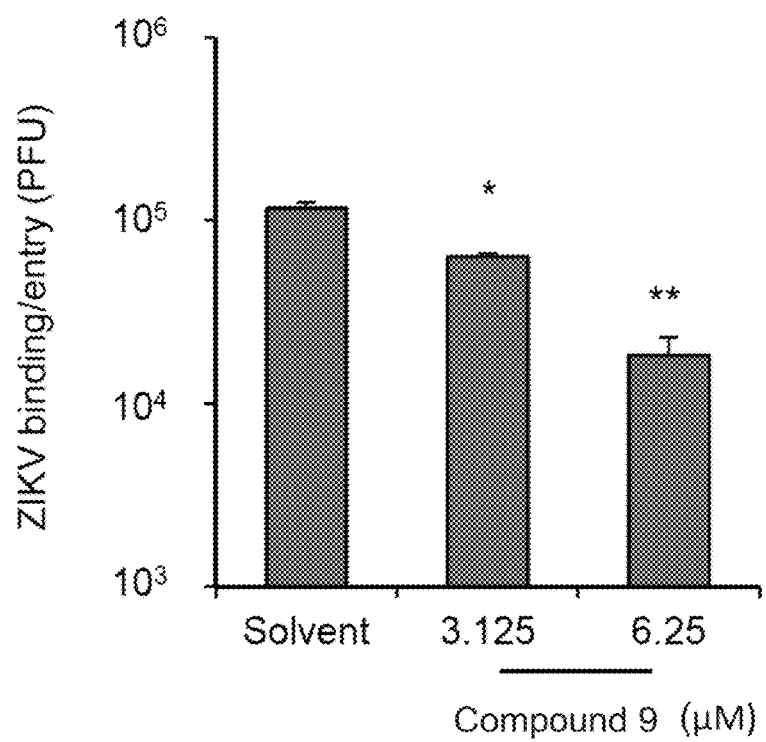
FIG. 3B shows the level of ZIKV binding to and entry into BE(2)C cells in the absence or presence of compound 9 at the indicated doses; * and ** indicate $P<0.05$ and $P<0.01$, respectively, based on student T-test compared with solvent control.

To investigate whether compound 9 displays the antiviral effect in the early or late stage of viral infection, BE(2)C cells were infected with DENV-2 or ZIKV (MOI, 1) in the absence or presence of the compound 9 at the indicated doses during (0-3 hpi) or after (3-24 hpi) virus adsorption. As shown in FIG. 3A, three hours of treatment with compound 9 during viral adsorption dose-dependently reduced viral-NS3 expression, indicating that compound 9 may tackle the early step of viral infection. Moreover, as shown in FIG. 3B, the level of ZIKV binding/entry was significantly reduced with compound 9 treatment.

Figure 3C:
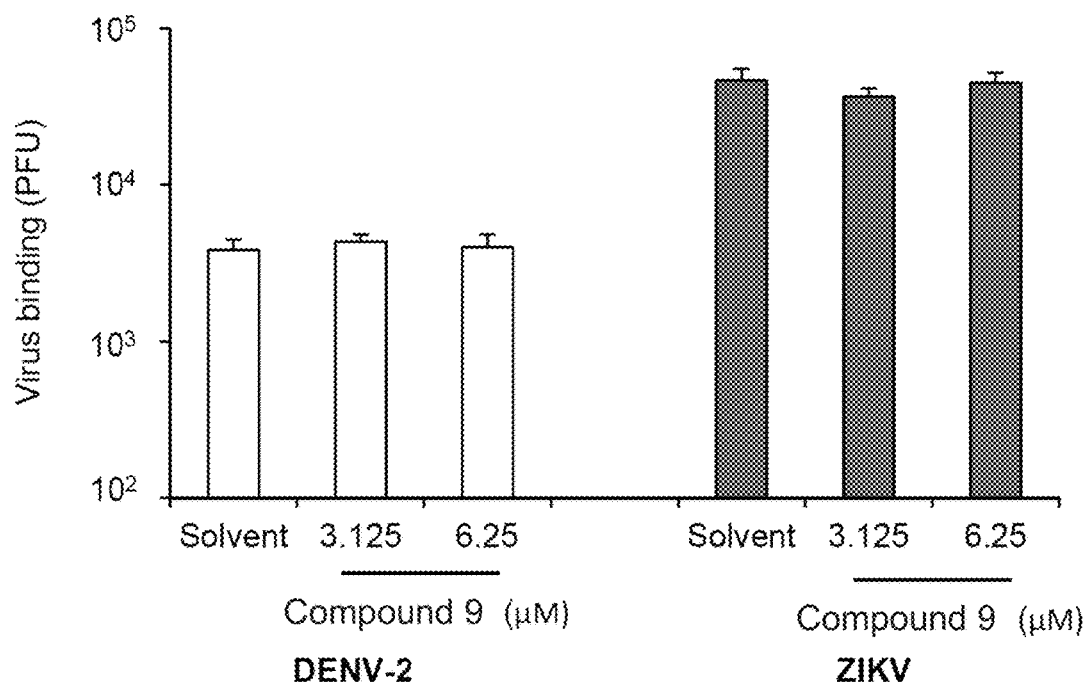
FIG. 3C shows the level of DENV-2 or ZIKV binding to BE(2)C cells in the absence or presence of compound 9 at the indicated doses.
Figure 3D:
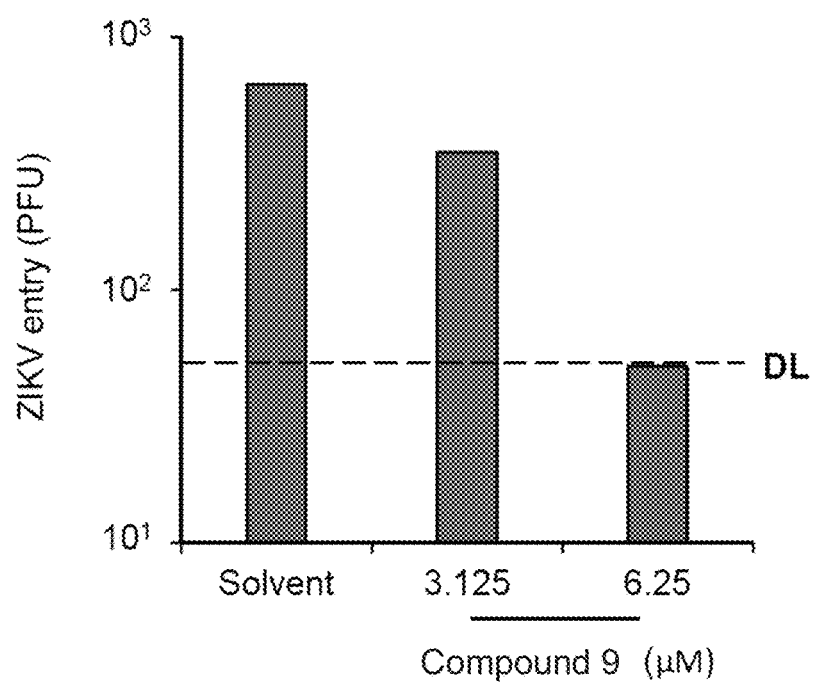
FIG. 3D shows the level of ZIKV entry into BE(2)C cells in the absence or presence of compound 9 at the indicated doses; the dashed line represents detection limit (DL)

To further dissect the effect of compound 9 on viral binding and entry, virus binding and virus entry assays were separately performed on BE(2)C cells in the absence or presence of the compound at various doses. As shown in FIG. 3C, treatment with compound 9 had no effect on DENV-2 or ZIKV binding to cells. However, as shown in FIG. 3D, the level of DENV-2 and ZIKV entry were significantly reduced with compound 9 treatment in a dose-dependent manner. Thus, the antiviral effect of compound 9 against DENV-2 and ZIKV infections is associated with viral entry.

Example 5

Compound 9 Improves the Survival of DENV-2 and ZIKV-Infected Mice

Stat1-deficient mice challenged with a mouse-adapted DENV-2 NGC-N strain or ZIKV were used as an infectious disease model to test whether compound 9 has an antiviral effect in vivo. Briefly, the mice were administered with PBS alone (n=5) or compound 9 (2, 4 or 8 mg/kg of body weight/day; n=5) in PBS at the time of infection (immediate treatment) or at 8 hours post-infection (8-hours-delay treatment), and then received the same dose of treatment until day 6 after infection.

Figure 4A:
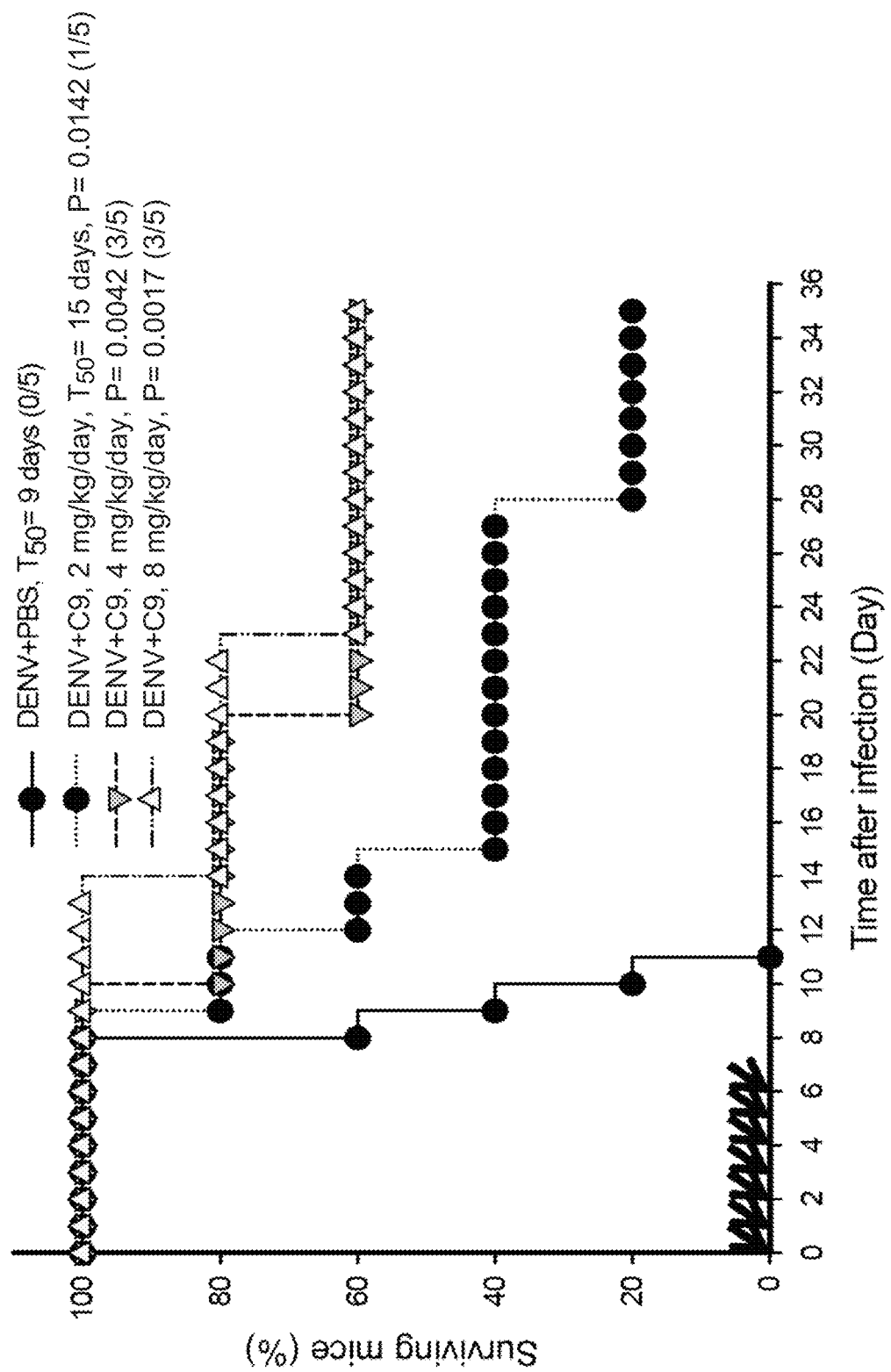
FIG. 4A shows the protective effect of the immediate treatment of compound 9 (denoted as C9) on the survival of DENV-2-infected Stat$^{-/-}$ mice; the day with treatment are marked by arrows.

As shown in FIG. 4A, immediate treatments with 8 or 4 mg compound 9/kg of body weight/day through oral administration during 6-day treatment period significantly improved the overall survival to 60% of DENV-2-infected mice. Notably, immediate treatment with a lower dose of compound 9 (2 mg/kg of body weight/day) significantly decreased animal mortality ($T_{50}$, 15 days versus 9 days for the vehicle control), with a minor effect on overall animal survival.

Figure 4B:
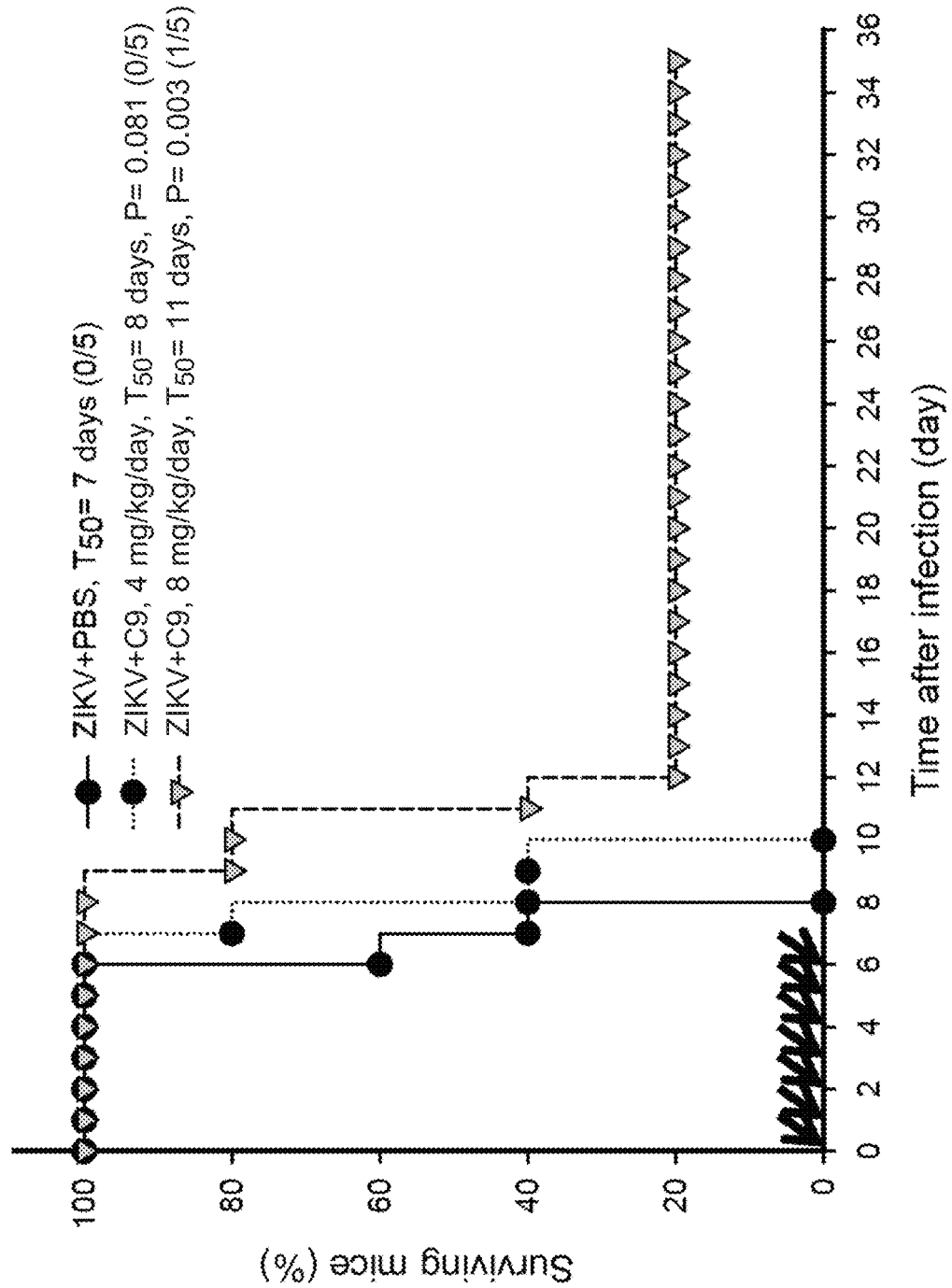
FIG. 4B shows the protective effect of the immediate treatment of compound 9 (C9) on the survival of ZIKV-infected Stat$^{-/-}$ mice; the day with treatment are marked by arrows.
Figure 4C:
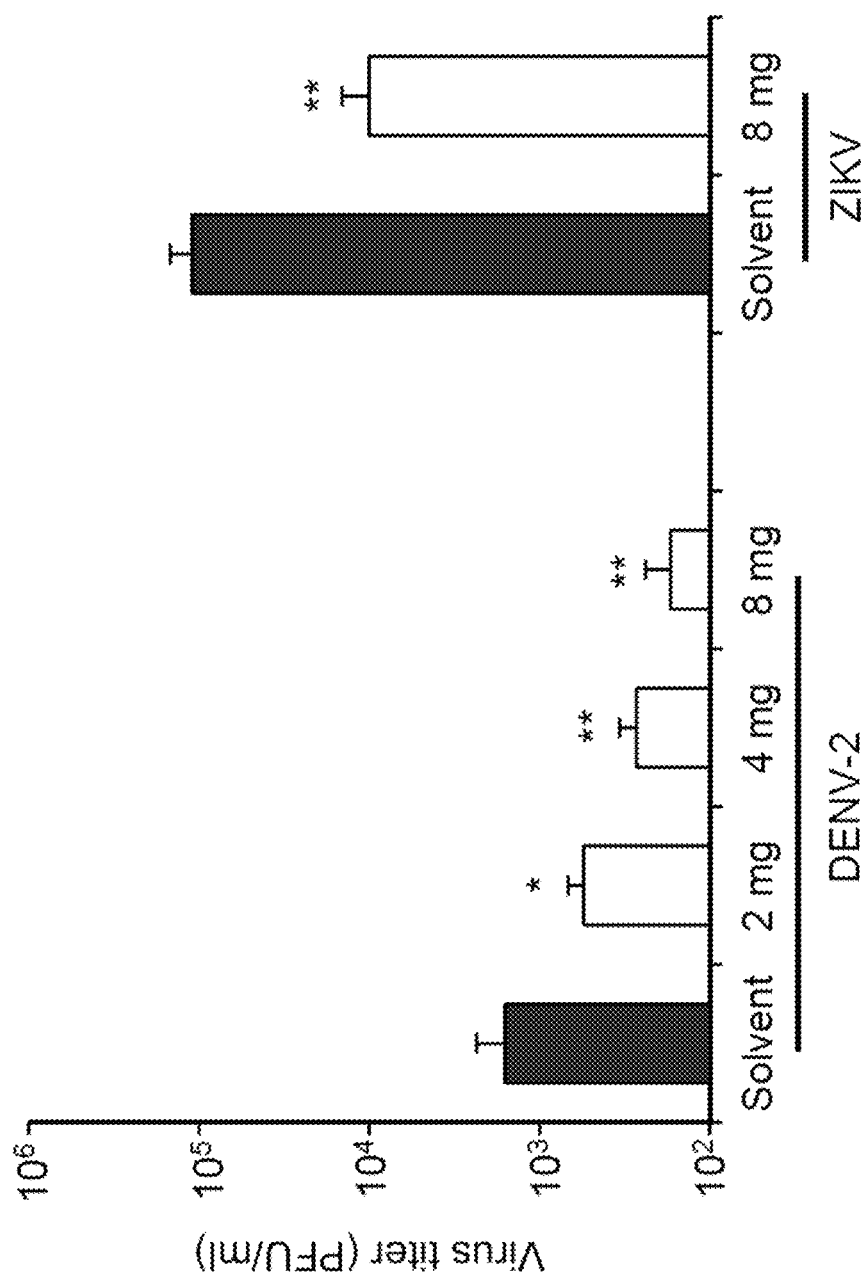
FIG. 4C shows virus titer of the serum samples collected from the differently treated mice of FIGS. 4A-4B; * and ** indicate $P<0.05$ and $P<0.01$, respectively, based on student T-test compared with solvent control.

As shown in FIG. 4B, immediate treatment with 8 mg compound 9/kg of body weight/day also significantly delayed ZIKV-induced lethality ($T_{50}$, 11 days versus 7 days for the vehicle control), but a lower dose of compound 9 (4 mg/kg of body weight/day) did not improve the overall survival. Furthermore, as shown in FIG. 4C, treatments with compound 9 significantly reduced the viral load of DENV-2 or ZIKV-infected mice in a dose-dependent manner. Thus, consistent with the mouse survival results, viral load data demonstrated the antiviral activity of compound 9 against DENV-2 and ZIKV infections.

Figure 4D:
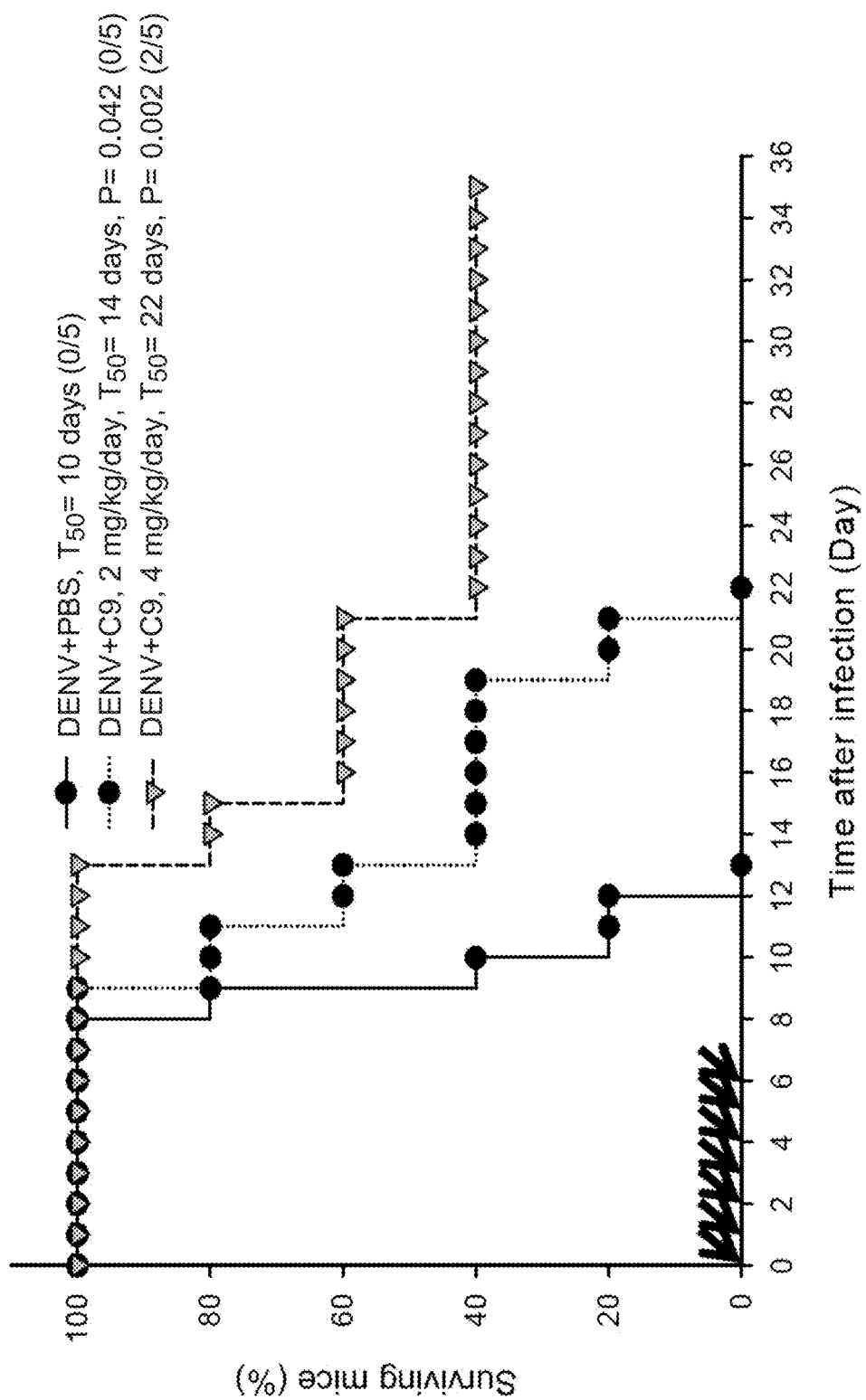
FIG. 4D shows the protective effect of 8-hours-delay treatment of compound 9 (C9) on the survival of DENV-2-infected Stat1$^{-/-}$ mice; the day with treatment are marked by arrows.
Figure 4E:
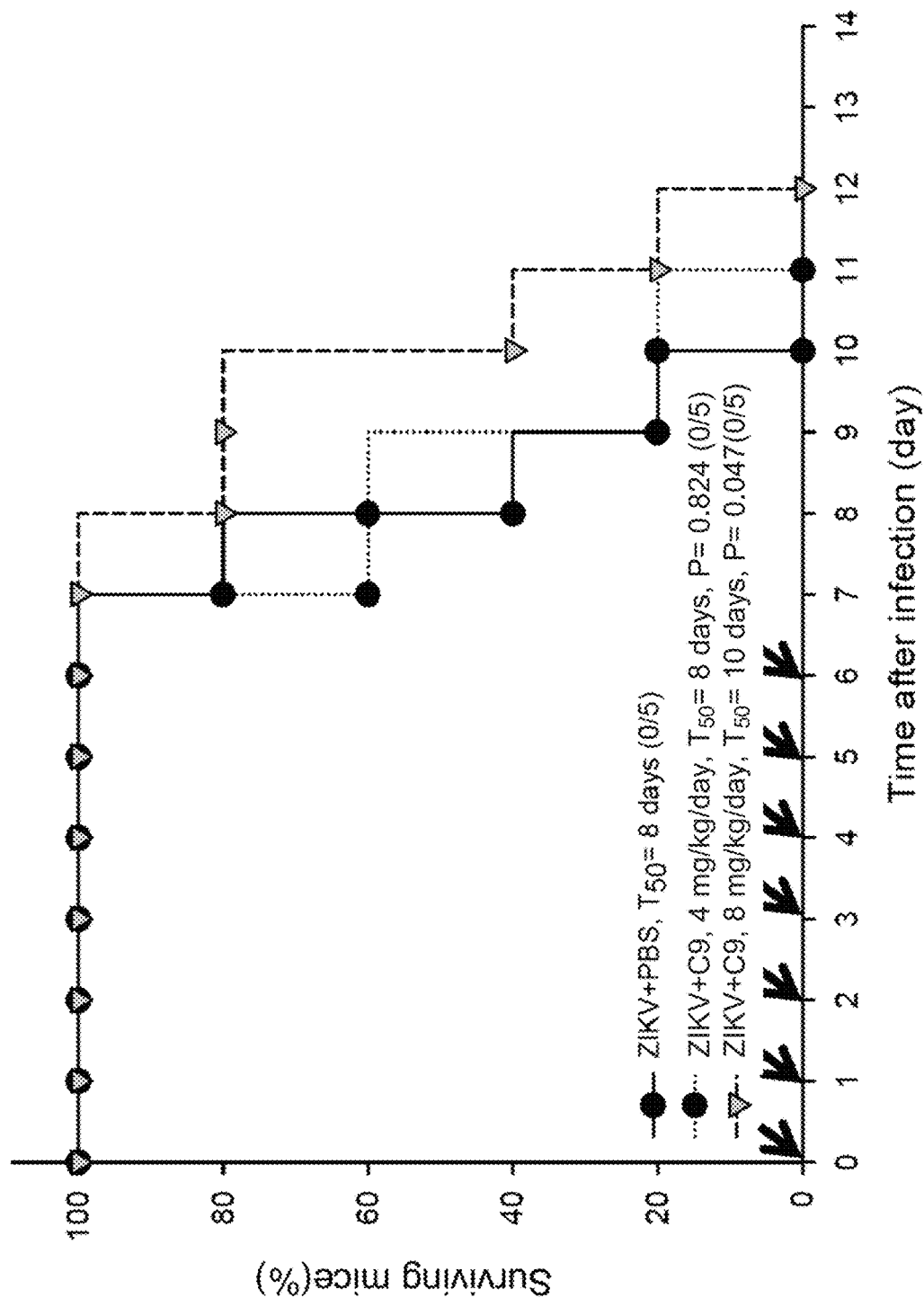
FIG. 4E shows the protective effect of 8-hours-delay treatment of compound 9 (C9) on the survival of ZIKV-infected Stat$^{-/-}$ mice; the day with treatment are marked by arrows.

The treatment starting from 8 hours after infection and ending at day 6 after infection (8-hours-delay) was performed to monitor the antiviral effect of compound 9 in the therapeutic mode of treatment. As shown in FIG. 4D, treatment with 2 mg compound 9/kg of body weight/day was sufficient to significantly improve the median survival time of DENV-2-infected mice ($T_{50}$, 14 days versus 10 days for the vehicle control). Moreover, treatment with a higher dose of compound 9 (4 mg/kg of body weight/day) protected 40% of DENV-2-infected mice from mortality and further increased the animal survival time ($T_{50}$, 22 days versus 10 days for the vehicle control). However, as shown in FIG. 4E, 8-hours-delay treatment with compound 9 had a minor effect on the overall survival of ZIKV-infected mice. Treatment with 8 mg compound 9/kg of body weight/day only improved the $T_{50}$ to 10 days. The different virulence and/or viral pathogenesis between DENV-2 and ZIKV in Stat1-deficient mice may contribute to the different effectiveness of compound 9 to improve the animal survival. Intriguingly, the inhibitory effect of compound 9 on the entry step of DENV-2 and ZIKV infection may explain a better efficacy of compound 9 given immediately than 8 hours after infection. Taken together, these data suggest that compound 9 has antiviral potency against DENV-2 and ZIKV infection in mammals.

Example 6

Inhibitory Effect of Compound 9 and Analogs Thereof on CaMKII Activity

Figure 5A:
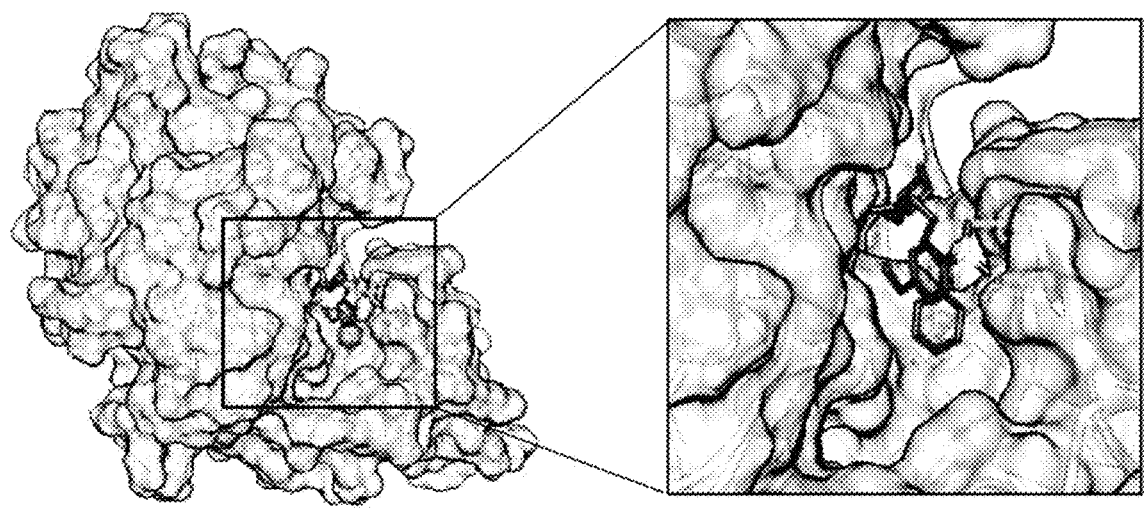
FIG. 5A shows the docking conformation of compound 9 in CaMKII.
Figure 5B:
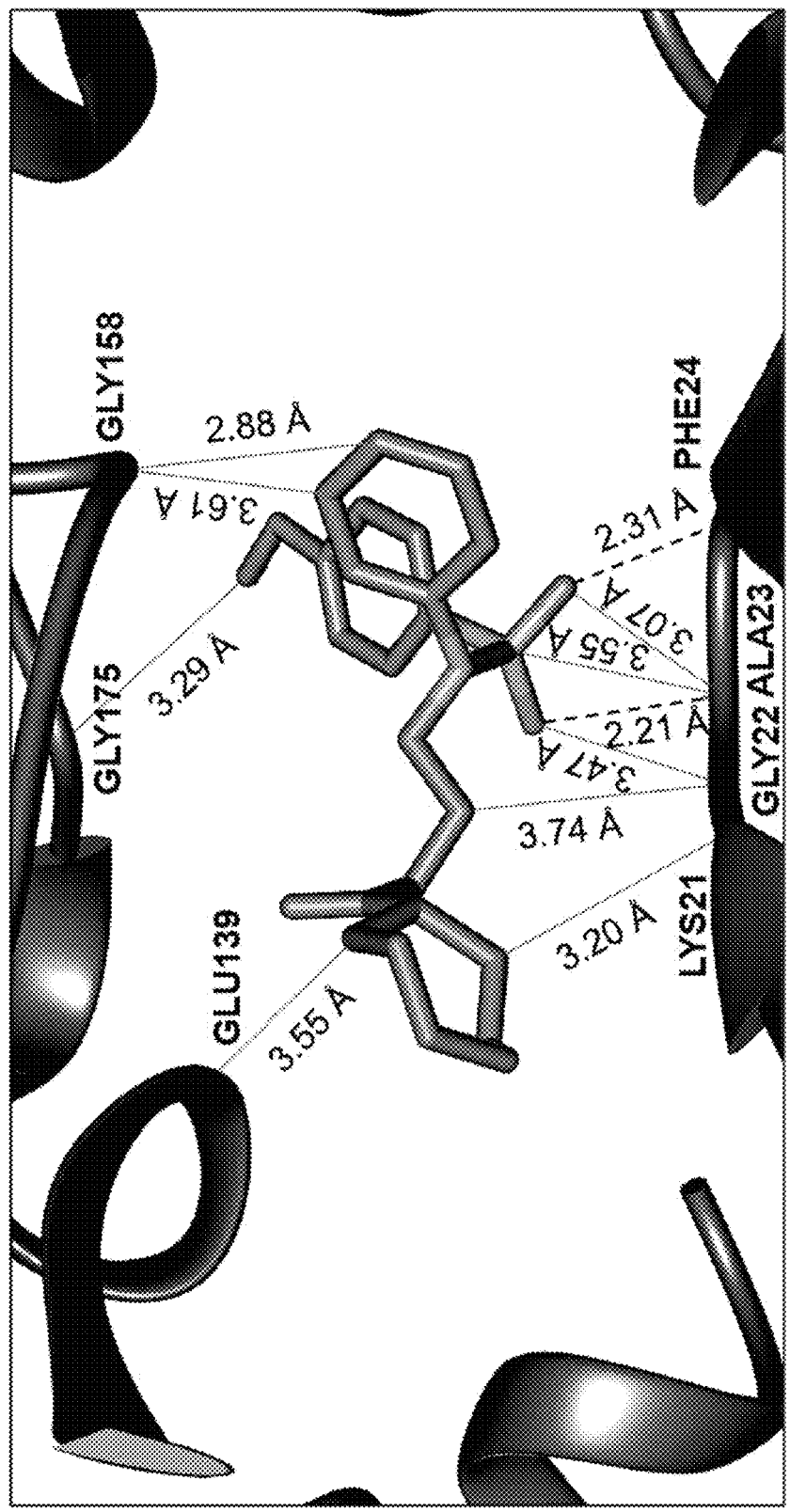
FIG. 5B shows the hydrogen bonds (dashed line) and hydrophobic interactions (solid line) between compound 9 and the indicated amino acid residues of CaMKII.

Molecular docking was performed to predict the interaction between compound 9 and CaMKII. As shown in FIG. 5A, compound 9 bound at the interface between the N-loop and C-loop of the CaMKII kinase domain. As shown in FIG. 5B, binding analysis revealed hydrogen-bond interactions between compound 9 and Ala23 (2.21 Å) and Phe24 (2.31 Å) of CaMKII. In addition, compound 9 was suggested to interact with Lys21, Gly22, Glu139, Gly175, and Gly158. Notably, Lys21, Gly22, and Phe24 are the residues located within the ATP-binding site of CaMKII. Furthermore, mutation of Glu139 of CaMKII resulted in a poor substrate affinity, because the residue is in a substrate-binding site. These data indicate that compound 9 may interfere ATP and substrate binding to CaMKII.

Figure 6A:
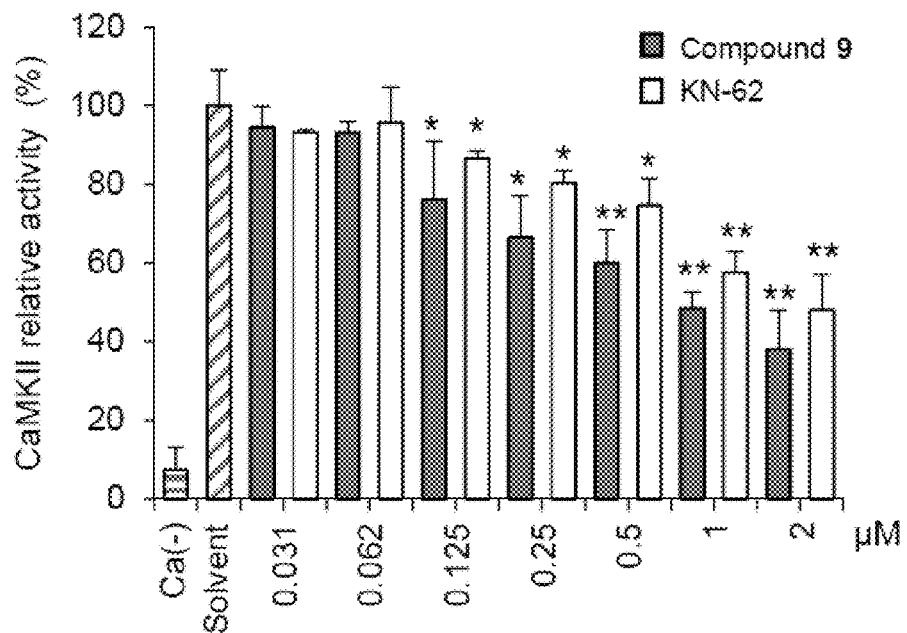
FIG. 6A shows the inhibitory effect of compound 9 and KN-62 on CaMKII activity; * and ** indicate $P<0.05$ and $P<0.01$, respectively, based on student T-test compared with solvent control.
Figure 6B:
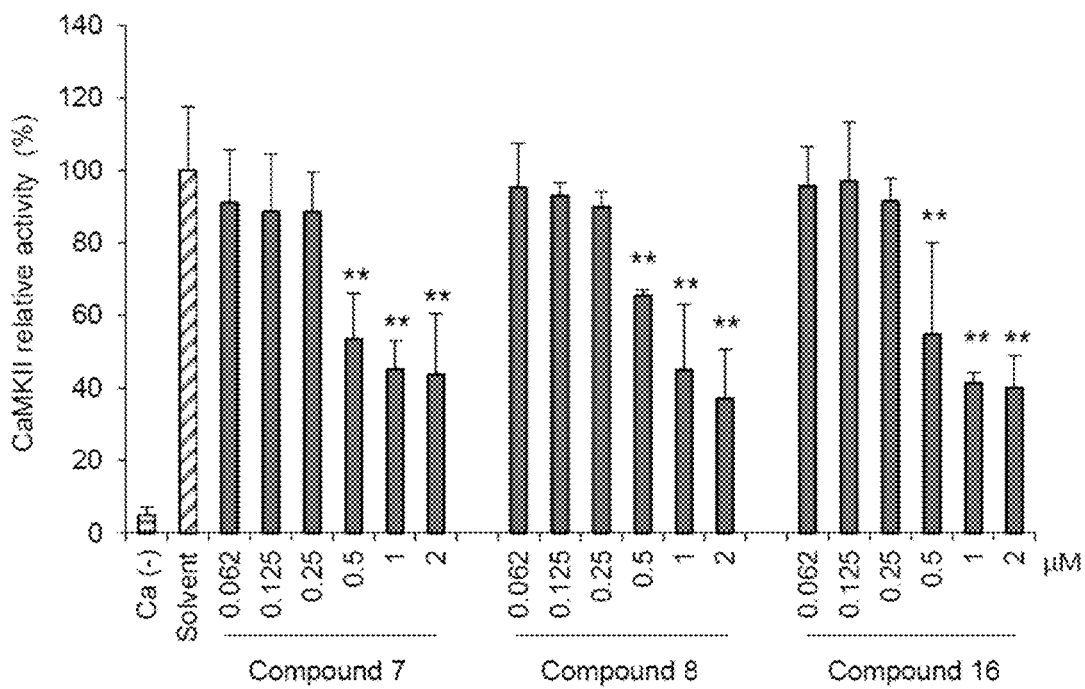
FIG. 6B shows the inhibitory effect of compounds 7, 8, and 16 on CaMKII activity; * and ** indicate $P<0.05$ and $P<0.01$, respectively, based on student T-test compared with solvent control.

To validate whether compound 9 and its analogs such as compounds 7, 8, and 16 inhibit CaMKII activity, a biochemical assay was performed of to measure the activity of purified human CaMKII in the absence or presence of these compounds. As shown in FIG. 6A, the activity of CaMKII was poorly observed in the absence of calcium ion (denoted as Ca(−)); compound 9 and KN-62, a commercial CaMKII inhibitor, significantly reduced CaMKII activity in a dose-dependent manner with an $IC_{50}$ of about 0.79 µM and 1.03 µM, respectively. As shown in FIG. 6B, compounds 7, 8 and 16 also significantly reduced CaMKII activity with an $IC_{50}$ of about 0.6 µM, 0.8 µM, and 0.7 µM, respectively.

From the above description, one skilled in the art can easily ascertain the essential characteristics of the present disclosure, and without departing from the spirit and scope thereof, can make various changes and modifications of the present disclosure to adapt it to various usages and conditions. Thus, other embodiments are also within the claims.

What is claimed is:

1. A compound which is represented by formula (I):

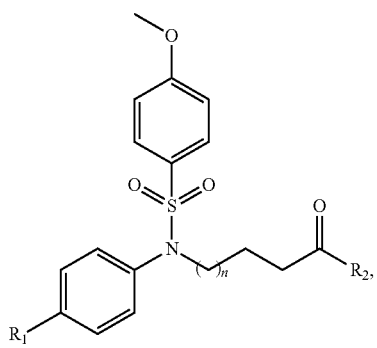

(I)

wherein $R_1$ is hydrogen, cycloalkyl having 3 to 7 carbon ring atoms, heterocycle having 2 to 8 carbon ring atoms and at least one heteroatom selected from the group consisting of nitrogen, oxygen, and sulfur, or aryl having 2 to 3 rings each with 4 to 6 ring atoms; or $R_1$ together with the phenyl ring to which $R_1$ is attached form a fused bicyclic carbocycle having 8 to 10 carbon ring atoms;

$R_2$ is cycloalkyl having 4 to 10 carbon ring atoms, or heterocycle selected from the group consisting of thiazole, imidazole, tetrazole, imidazolidine, imidazoline, isoxazole, and benzimidazole; and n is 1, 2, 4, or 6.

2. The compound of claim 1, wherein $R_1$ is hydrogen and n is 1.

3. The compound of claim 2, which is represented by one of the following formulas:

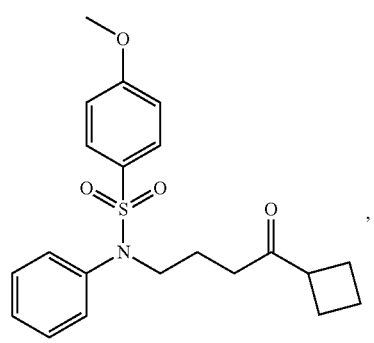

7

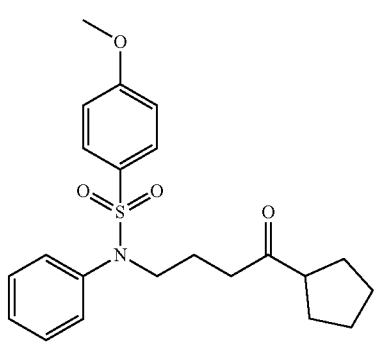

8

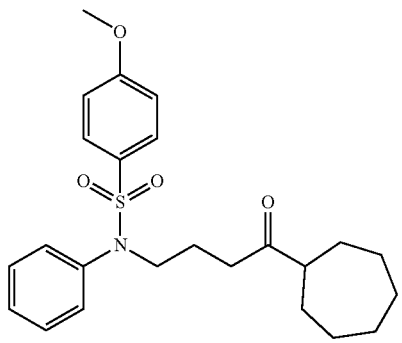

9

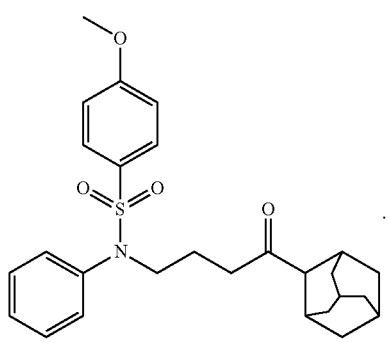

10

4. The compound of claim 1, wherein $R_1$ is hydrogen; $R_2$ is cycloheptyl; and n is 2, 4, or 6.

5. The compound of claim 1, wherein $R_2$ is cycloheptyl and n is 1.

6. The compound of claim 5, which is represented by one of the following formulas:

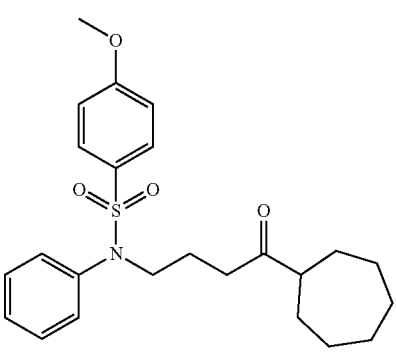

9

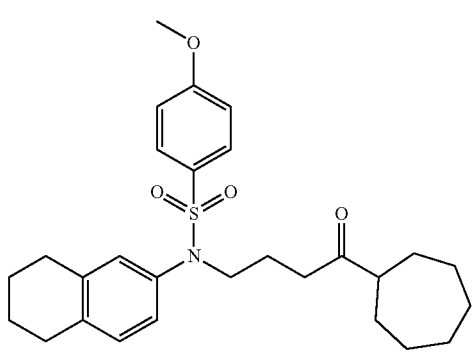

15

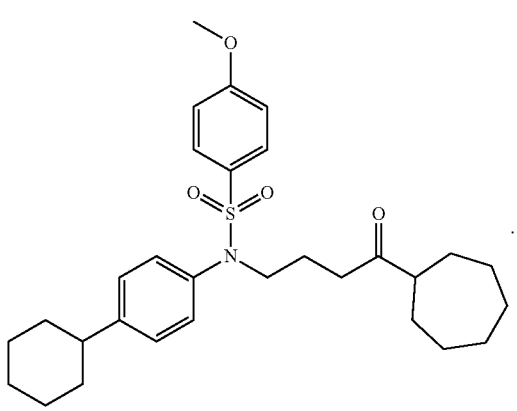
16
7. A pharmaceutical composition, comprising a compound of claim 1 and a pharmaceutically acceptable carrier.
* * * * *

SEQUENCE LISTING

<160> NUMBER OF SEQ ID NOS: 1

<210> SEQ ID NO 1
<211> LENGTH: 313
<212> TYPE: PRT
<213> ORGANISM: Homo sapiens

<400> SEQUENCE: 1

```
Met His His His His His Ser Ser Gly Val Asp Leu Gly Thr Glu
1               5                   10                  15

Asn Leu Tyr Phe Gln Ser Met Tyr Gln Leu Phe Glu Glu Leu Gly Lys
            20                  25                  30

Gly Ala Phe Ser Val Val Arg Arg Cys Val Lys Val Leu Ala Gly Gln
            35                  40                  45

Glu Tyr Ala Ala Lys Ile Ile Asn Thr Lys Lys Leu Ser Ala Arg Asp
    50                  55                  60

His Gln Lys Leu Glu Arg Glu Ala Arg Ile Cys Arg Leu Leu Lys His
65                  70                  75                  80

Pro Asn Ile Val Arg Leu His Asp Ser Ile Ser Glu Glu Gly His His
                85                  90                  95

Tyr Leu Ile Phe Asp Leu Val Thr Gly Gly Glu Leu Phe Glu Asp Ile
            100                 105                 110

Val Ala Arg Glu Tyr Tyr Ser Glu Ala Asp Ala Ser His Cys Ile Gln
            115                 120                 125

Gln Ile Leu Glu Ala Val Leu His Cys His Gln Met Gly Val Val His
    130                 135                 140

Arg Asp Leu Lys Pro Glu Asn Leu Leu Leu Ala Ser Lys Leu Lys Gly
145                 150                 155                 160

Ala Ala Val Lys Leu Ala Asp Phe Gly Leu Ala Ile Glu Val Glu Gly
                165                 170                 175

Glu Gln Gln Ala Trp Phe Gly Phe Ala Gly Thr Pro Gly Tyr Leu Ser
            180                 185                 190

Pro Glu Val Leu Arg Lys Asp Pro Tyr Gly Lys Pro Val Asp Leu Trp
            195                 200                 205

Ala Cys Gly Val Ile Leu Tyr Ile Leu Leu Val Gly Tyr Pro Pro Phe
            210                 215                 220

Trp Asp Glu Asp Gln His Arg Leu Tyr Gln Gln Ile Lys Ala Gly Ala
225                 230                 235                 240

Tyr Asp Phe Pro Ser Pro Glu Trp Asp Thr Val Thr Pro Glu Ala Lys
                245                 250                 255

Asp Leu Ile Asn Lys Met Leu Thr Ile Asn Pro Ser Lys Arg Ile Thr
            260                 265                 270

Ala Ala Glu Ala Leu Lys His Pro Trp Ile Ser His Arg Ser Thr Val
            275                 280                 285

Ala Ser Cys Met His Arg Gln Glu Thr Val Asp Cys Leu Lys Lys Phe
            290                 295                 300

Asn Ala Arg Arg Lys Leu Lys Gly Ala
305                 310
```